United States Patent
Biro et al.

(10) Patent No.: US 7,824,445 B2
(45) Date of Patent: *Nov. 2, 2010

(54) CORPECTOMY VERTEBRAL BODY REPLACEMENT IMPLANT SYSTEM

(76) Inventors: Ladislau Biro, 14 Michael Dr., Metuchen, NJ (US) 08840; Howard Cohen, 333 River St., Apt. 439, Hoboken, NJ (US) 07030; Mathew Cohen, 272 W. Park Ave., Long Beach, NY (US) 11561

( * ) Notice: Subject to any disclaimer, the term of this patent is extended or adjusted under 35 U.S.C. 154(b) by 385 days.

This patent is subject to a terminal disclaimer.

(21) Appl. No.: 11/974,653

(22) Filed: Oct. 15, 2007

(65) Prior Publication Data

US 2008/0103601 A1     May 1, 2008

Related U.S. Application Data

(60) Continuation-in-part of application No. 10/761,978, filed on Jan. 21, 2004, now Pat. No. 7,282,063, which is a division of application No. 10/072,163, filed on Feb. 7, 2002, now Pat. No. 6,719,796, which is a continuation of application No. 09/360,796, filed on Jul. 26, 1999, now Pat. No. 6,454,806.

(51) Int. Cl.
*A61F 2/44*     (2006.01)

(52) U.S. Cl. .................................. 623/17.15
(58) Field of Classification Search ... 623/17.11–17.16; 606/246, 248, 279
See application file for complete search history.

(56) References Cited

U.S. PATENT DOCUMENTS

| | | | | |
|---|---|---|---|---|
| 5,865,848 | A * | 2/1999 | Baker ....................... | 623/17.15 |
| 6,019,792 | A * | 2/2000 | Cauthen .................. | 623/17.14 |
| 6,176,881 | B1* | 1/2001 | Schar et al. ............... | 623/17.11 |
| 6,193,756 | B1* | 2/2001 | Studer et al. ............. | 623/17.15 |
| 6,344,057 | B1* | 2/2002 | Rabbe et al. ............. | 623/17.11 |
| 6,454,806 | B1* | 9/2002 | Cohen et al. ............. | 623/17.15 |
| 6,719,796 | B2* | 4/2004 | Cohen et al. ............. | 623/17.15 |
| 7,282,063 | B2* | 10/2007 | Cohen et al. ............. | 623/17.13 |
| 7,601,174 | B2* | 10/2009 | Kelly et al. ............... | 623/17.13 |
| 7,641,692 | B2* | 1/2010 | Bryan et al. ............. | 623/17.15 |

* cited by examiner

*Primary Examiner*—David Isabella
*Assistant Examiner*—Marcia Hoffman
(74) *Attorney, Agent, or Firm*—Walter J. Tencza, Jr.

(57) ABSTRACT

An improved artificial spinal implant system for replacing a disc or vertebral body that provides adjustability in height, and provides support and stability of the spine with proper lordosis or kyphosis, osseous-integration of the implant, and motion preservation (if desired) of the adjacent vertebrae while preserving the space. Motion preservation is achieved with compressible and/or tiltable artificial discs.

23 Claims, 31 Drawing Sheets

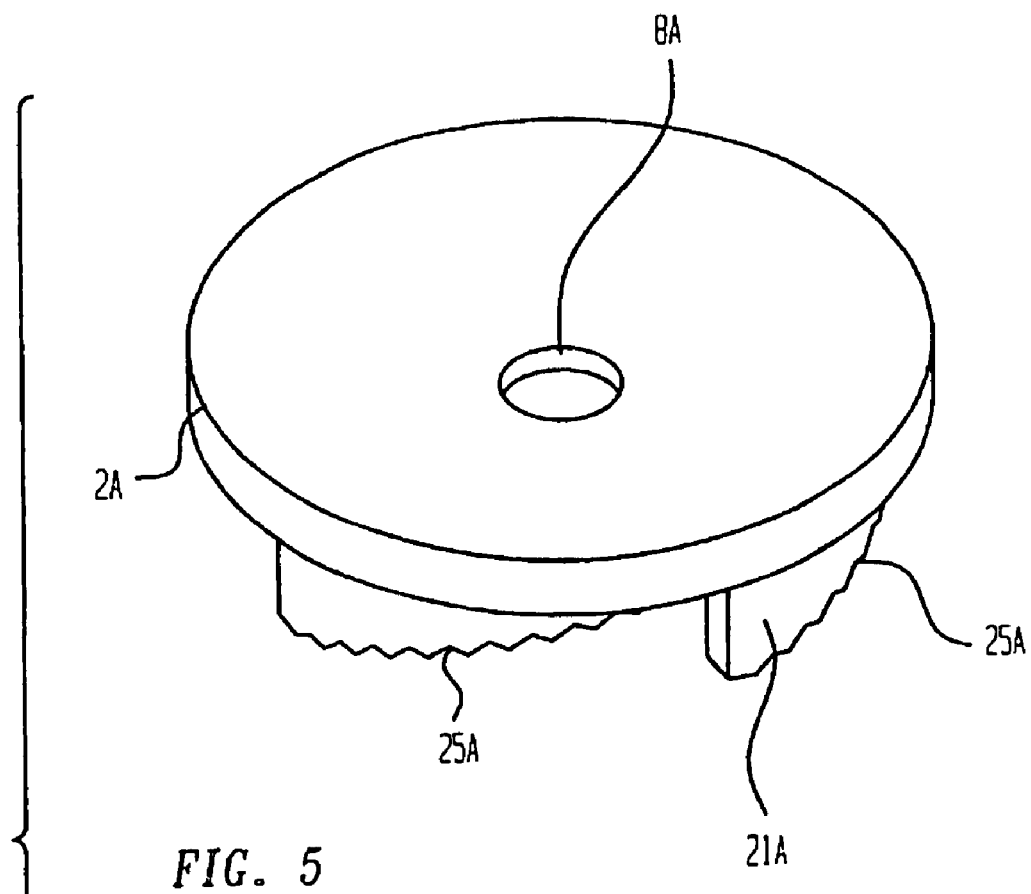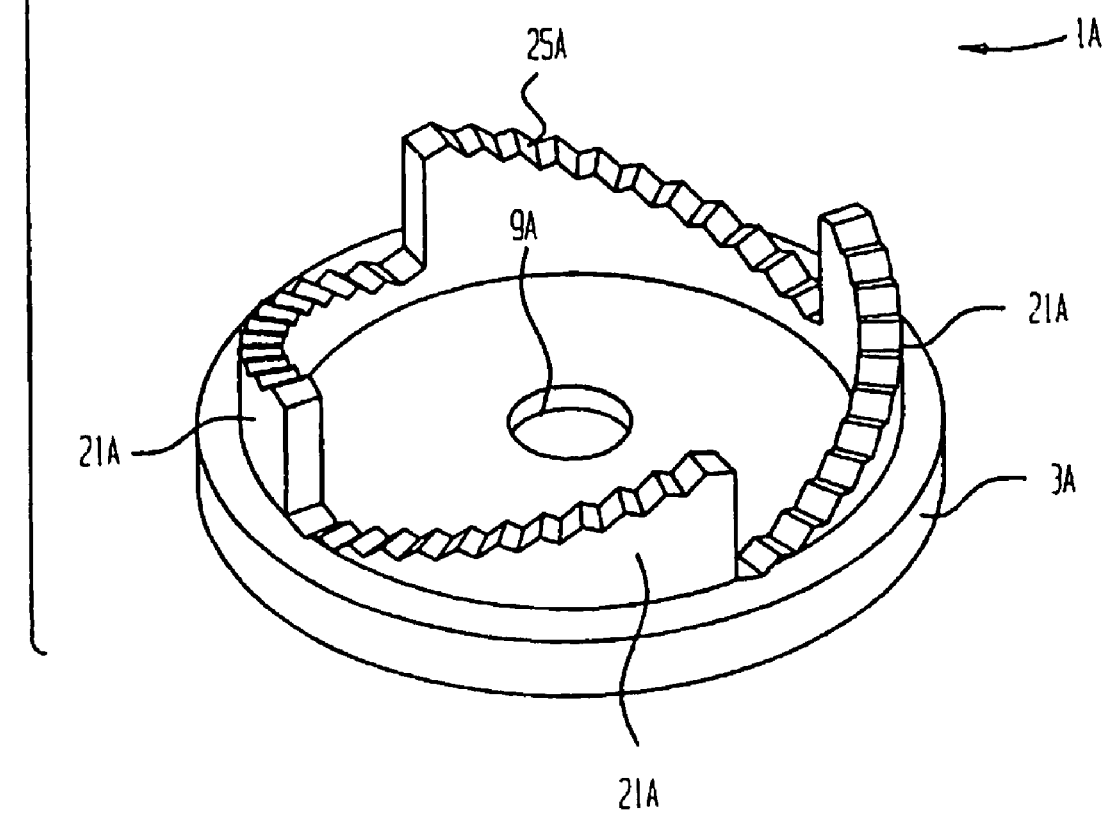
FIG. 5

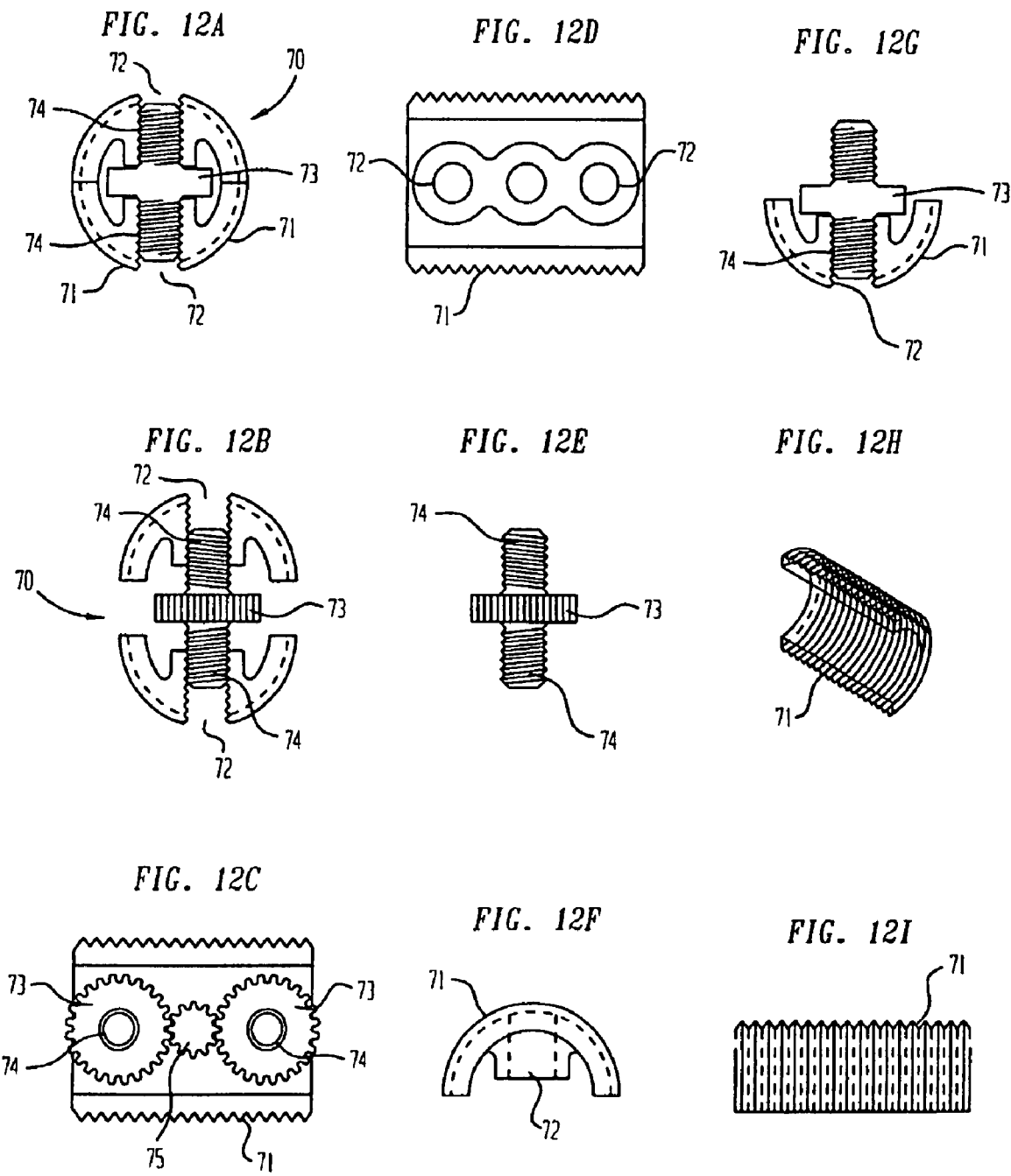

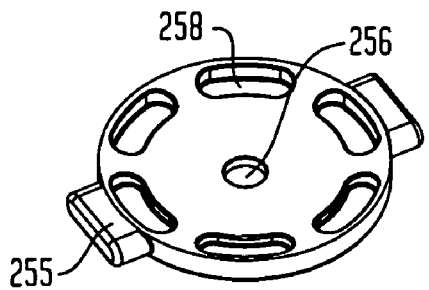
FIG. 30A
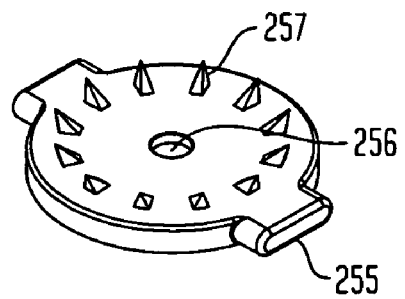
FIG. 30B
FIG. 30C
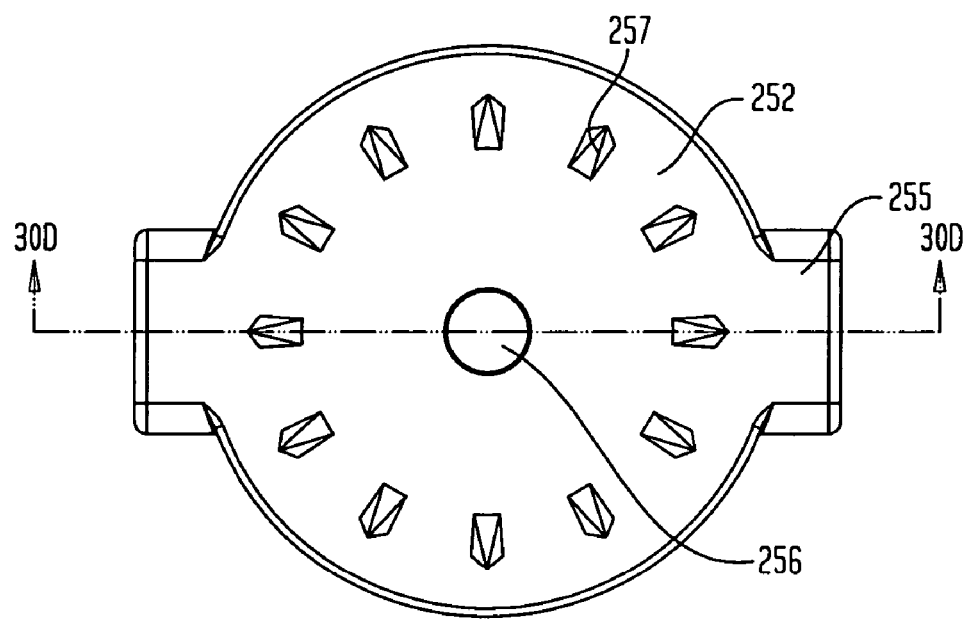
FIG. 30D
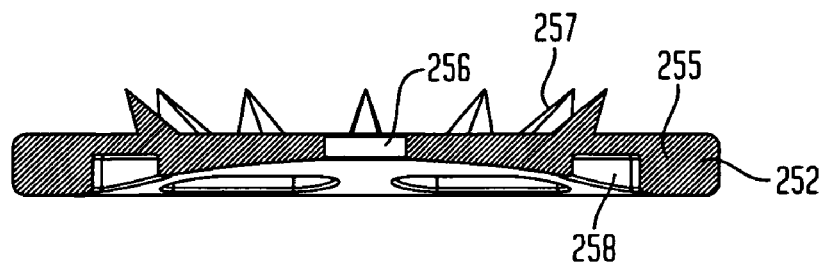

CORPECTOMY VERTEBRAL BODY REPLACEMENT IMPLANT SYSTEM

CROSS-REFERENCE TO RELATED APPLICATION

This is a continuation-in-part of pending application Ser. No. 10/761,978, filed on Jan. 21, 2004, and issued as U.S. Pat. No. 7,282,063 on Oct. 16, 2007, which is a divisional application of Ser. No. 10/072,163, filed on Feb. 7, 2002, and issued as U.S. Pat. No. 6,719,796 on Apr. 13, 2004, which is a continuation application of Ser. No. 09/360,796, filed on Jul. 26, 1999, and issued as U.S. Pat. No. 6,454,806 on Sep. 24, 2002, all of which are hereby incorporated by reference.

FIELD OF INVENTION

The present invention relates to an improved artificial spinal surgical prosthesis such as an improved artificial disc and corpectomy prosthetic implant that promotes inter-vertebral fusion and motion preservation. In particular, apparatus for achieving stability and functionality of adjacent vertebrae while preserving the inter-disc space following discectomy by internal fixation or fusion of the engaging and bearing endplates. In an alternate embodiment of the present invention, the corpectomy vertebral body replacement implant system utilizes artificial discs at one or more locations to establish normal height, support and stability of the spine with proper lordosis or kyphosis, osseous-integration of the artificial disc endplates with motion preservation of the adjacent vertebrae while preserving the space following corpectomy by internal fixation and/or fusion.

BACKGROUND OF THE INVENTION

Fusion is a commonly performed procedure for bonding adjacent bone structures of the spine and for those not adjacent, providing long term replacement by fixation and support to treat degenerative or deteriorated disorders of the spine.

An inter-vertebral disc is a ligamentous cushion disposed between vertebrae and as a result of injury, disease or other disorders may deteriorate in part or in whole, thereby leading to mechanical instability and painful disc translocations and often necessitating bed rest or hospitalization. If left untreated possible subsequent involvement of adjacent nerves and muscular involvement may occur. In such cases, if treatment is delayed, permanent damage to the nerves may result in muscular atrophy and severe dysfunction.

Procedures for disc surgery may involve partial or total excision of the injured disc portion and replacement with biocompatible devices of bone, elastomeric or other bio-compatible materials.

Corpectomy is a procedure performed to relieve pain caused by fractured vertebrae and subsequent decompression of the spinal cord when the entire anterior body of the vertebrae is involved. This is most common in vertebral fractures referred to as Burst fractures and usually occurs from severe trauma, such as a motor vehicle accident or fall from a height resulting in a great deal of force directed vertically onto the spine causing a vertebral body to be crushed in all directions. A vertebral body that is crushed in such instances requires immediate surgical intervention once the patient has been stabilized so as to prevent irreversible damage to the spinal cord. Other fractures of the vertebral body may occur only in the anterior portion and are known as compression fractures, and as such do not require decompression of the spinal cord. In such instances, only a portion of the vertebral body and the entire adjacent vertebral discs are removed and an implant may be placed between the adjacent vertebrae for fusion to occur in restoring the required support and curvature of the spine. Corpectomy may also be performed in individuals having bone spurs that put pressure on the nerves or spinal cord. Other indications for a corpectomy surgical procedure are diseases due to infection or malignant tumors resulting in degeneration of the vertebral bone body. Corpectomy may also be the surgical method of choice in treatment of kyphosis or lordosis in the cervical, thoracic and lumbar areas so as to restore the normal curvature of the spine.

Previous procedures for corpectomy involved total or partial excision of the diseased or injured vertebral body along with the adjacent vertebral discs and replacement with biocompatible devices of bone, or bone-like material or artificial biocompatible implants that may be adjustable or non-adjustable for fusion to the adjacent vertebrae.

Back in 1983, Dubousset, with the assistance of Graf and Hecquet, defined the three-dimensional relationship of the spine in space and states: "after fusion of the spine, the resulting balance is determined by the unfused segments of the spine remaining mobile, not by the fused segments" and continues by stating "the dynamic changes above and below proposed end vertebrae of a spinal fusion are more important in determining final balance than what occurs within the fused segments." A publication entitled "Journal of Neurosurgery; Spine," September 2004 Volume 1 Number 2, in further support of Dubousset's Three-Dimensional Theory states: "[t]he normal motion of a lumbar segment includes independent translation and rotation in all three planes of motion (flexion-extension, lateral bending, and axial rotation). Normal motion is often represented as a factor of coupled motion in two planes. The implant-related geometrical configuration and material would determine the static configuration, dynamic motion, schematics, and any constrained nature of the motion. The exact placement of the artificial lumbar disc in the disc space is determined by its biomechanical design." Although these references are directed to artificial disc biomechanics, they are also directly related to corpectomy which normally involves the removal of the diseased vertebral body and its two adjacent vertebral discs. Corpectomy results in a significantly large space between the remaining intact adjacent vertebral bodies and fusion of the space results in extremely heavy loads and shearing forces directed at the fused sites and at the implants used for fusion at said sites. An article entitled "Prediction of Mechanical Behaviors at Interfaces between Bone and Two Interbody Cages of Lumbar Spine Segments," identifies that micromotion at bone-implant interfaces can hinder bone growth into the surface pores of an implant and that relative micromotion is sensitive to the friction coefficient of the interfaces, the bone density, and the loading conditions. An article published in Spine 2000 Dec. 1, entitled "2000 Volvo Award Winner in Biomechanical Studies Monitoring in Vivo Implant Loads with a Telemeterized Internal Spinal Fixation Device" identifies that implant loads often increased shortly after anterior interbody fusion was performed and that a flexion bending moment acts on an implant even with the body in the relaxed lying position.

Early Techniques

Bone material was simply disposed between the adjacent vertebrae, typically at the posterior aspect of the vertebrae and the spinal column was stabilized by way of a plate or rod connecting the involved vertebrae. However, the use of bone may require undesired additional surgery and is of limited availability in its most useful form. In addition, the risk of infection and rejection is a significant consequence. In any event, bone is only marginally structural and with bone it is difficult to stabilize both the implant against dislodgment and stabilize the adjacent vertebrae. It becomes desirable to find solutions for stabilization of an excised disc space by fusing an artificial disc to the vertebrae between their respective end plates so that said vertebra can function in a relatively normal fashion by movement subsequent to load forces placed upon the spine. Following corpectomy, it is also desirable to find solutions for stabilization of the space resulting from the excised discs and diseased vertebral body by an implant system that fuses one or more artificial discs of the implant to the vertebrae between their respective end plates of the artificial discs so that the vertebrae can function in a relatively normal fashion by movement subsequent to load forces placed upon the spine. And more particularly to the rigid adjustable vertebral intermediate body to which the artificial discs are attached.

PRIOR ART

A review of the prior art clearly reveals attempts to achieve such solutions in two distinct areas in replacing an excised disc and/or vertebral body, namely:

I. Static non-adjustable inter-body fusion devices that can act as an artificial disc or can act to support the spine and restore its normal curvature.

II. Adjustable inter-body fusion devices that can restore and stabilize varying heights of the intra-discal space that can act as an artificial disc or can act to support the spine and restore its normal curvature.

I. Static Inter-Body Fusion Devices

An extensive number of static inter-body artificial disc fusion devices commonly called "cages" have evolved for replacement of a damaged disc while still maintaining stability of the disc inter-space between the adjacent vertebrae while acting as an artificial disc.

However, existing static inter-body artificial disc fusion devices encountered some problems. They require extensive distraction, drilling, boring or tapping of the end plates which sometimes results in removal of an excessive amount of supporting bone with possible damage to adjacent structures. Moreover, threads of the implant or cage may inadvertently engage the prepared threads of the vertebrae in an improper manner so as to cause a misalignment of the vertebrae in an anterior-posterior direction as well as laterally. If a second cage is needed, it involves the drilling, boring or tapping of the vertebral end plates for both cages so that the threads direct the cages into their proper respective positions. Such preparation requires highly skilled precision that may not be afforded or attainable under normal working conditions.

When a second cage is inserted, due to the unevenness of the vertebral end plates concave engaging surfaces, an unwanted increase in the inter-vertebral space may result in the loosening and possible dislodgment of the initially placed implant cage.

The anatomical configurations of the vertebrae necessitates that the two cages be positioned at an angle in respect to each other so as to be totally within the confines of the lateral borders of the vertebrae involved.

Use of tapered cages that are dimensionally greater in height anteriorally than posteriorly so as to provide the proper lordosis when such cage implants are employed creates complications. When the posterior approach is utilized and drilling, boring or tapping is necessary for placing threads on the vertebral end plates, difficulties exist in creating threads that will have a pitch compatible with those exhibited by the threads of such cages. These cages are self-tapping to some degree and may result in the unwanted excessive removal of bone from the posterior portion of the lumbar segments where the lordosis is greatest.

Drilling and other types of preparation of the vertebral end plates may result in the removal of excessive amounts of supporting bone, and may cause the cage implants to rest upon the cancellous portion of the vertebrae. In such instances subsidence of the cages may result in the settling into said vertebrae resulting in a decreased inter-vertebral space other than that desired with subsequent complications of stabilization, pain and discomfort.

II. Adjustable Inter-Body Fusion Devices

An extensive number of adjustable inter-body artificial disc fusion devices commonly called "cages" have evolved for replacement of a damaged disc while still maintaining stability of the disc inter-space between the adjacent vertebrae while acting as an artificial disc.

These are designed for restoring and maintaining the intervertebral space thereby providing for the normal contour and function of the fused spinal segments. Once the disc is removed, the normal lordotic or kyphotic curvature is eliminated and adjustable inter-body fusion implants are employed for re-establishing the proper curvature and stabilization of the spine.

Height adjustable inter-body fusion artificial disc and corpectomy devices have universal applicability and may eliminate the need for surgical preparation of the vertebral end plates such as contouring of bone and drilling, boring and tapping of said vertebral end plates. Such devices restore and preserve the inter-space or enlarged inter-vertebral space following corpectomy and the integrity of the adjacent vertebrae thereby making the selection of the proper implant size easier. This results in preservation of the highly specialized weight bearing cortical bone thereby preventing end plate perforation into the highly vascular cancellous bone marrow and unwanted subsequent subsidence as well as limiting bleeding that may result in many complications due to excessive blood loss (e.g. hypoglycemic shock, transfusion, and possible diseases such as hepatitis and Acquired Immune Deficiency Syndrome, etc.). Another advantage of such devices is the elimination of incorrect implant size selection as no significant amount of bone is removed and the correct size implants are easily fitted to restore the proper inter-space between the vertebrae following discectomy or corpectomy. Most existing height adjustable interbody fusion corpectomy devices are deficient in their ability to selectively and incrementally adjust the opposing individual vertebrae to their proper height. This may result in over-distraction of one of the vertebrae when using the existing adjustable corpectomy devices.

DESCRIPTION OF THE RELATED ART

The following patents and patent application publications disclose Static Inter-Body Fusion Devices: U.S. Pat. Nos. 6,827,740; 6,652,585; 6,635,086; 6,607,558; 6,576,016; 6,533,818; 6,478,823; 6,447,547; 6,440,168; 6,419,704; 6,402,785; 6,395,032; 6,325,827; 6,299,644; 6,264,656; 6,179,874; 6,249,650; 6,162,525; 6,136,031; 6,123,705; 6,093,205; 6,039,763; 6,001,130; 5,893,889; 5,785,710; 5,782,919; 5,766,253; 5,609,636; 5,425,772; 4,878,915; 4,501,269; 4,961,240; and 5,055,104; U.S. Patent Application Publication Nos. 2005/0228501; 2006/0116770; 2005/0107878; 2005/0085910; 2005/0096744; 2005/0060034; 2004/0186589; 2004/0023308; and 2002/0083749.

The following patents and patent application publications disclose Adjustable Inter-Body Fusion devices: U.S. Pat. Nos. 7,008,421; 6,991,653; 6,921,403; 6,866,682; 6,582,431; 6,344,057; 6,299,644; 6,200,348; 6,193,756; 6,176,881; 6,159,244; 6,159,211; 5,989,290; 5,865,848; 5,782,832; 5,766,199; 5,702,455; 5,665,122; 5,609,635; 5,336,223; and 5,306,310; U.S. Patent Application Publication Nos. 2005/0096744; 2006/0116768; 2006/0116770; and 2004/0186569.

It is important to note that the prior art devices do not provide for flexibility, compressibility and/or tilting when employing artificial discs as part of their corpectomy devices in attempting to provide motion preservation of the intact adjacent vertebrae. This results in heavy loads and shearing forces imparted upon said devices which may result in their expulsion or dislodgement and even breakage from the adjacent vertebrae. Furthermore, the lack of flexibility and compressibility for providing motion preservation may create further damage to adjacent discs of adjacent vertebrae that are above and below the site being restored as well as damage to the rigid adjustable intermediate vertebral structure.

Most prior art corpectomy devices used to stabilize and reconstruct large vertebral body defects rely upon fusion of the adjacent vertebrae without providing for motion preservation. Devices such as VERTE-SPAN by Medtronic of Tennessee, X-PAND by Globus Medical of California, NGAGE SURGICAL MESH SYSTEM by Blackstone Medical of New Jersey and the OCELOT STACKABLE CAGE SYSTEM by Depuy Spine of Massachusetts, represent fusion devices for use following corpectomy for stabilizing the anterior column of the spine as alternatives to plate and screw or rod and screw constructs that were formerly used. The size and shape of implants to stabilize the anterior column is quite challenging compounded by the fact that surgeons are often required to reconstruct the sagittal alignment of the spine by restoring the appropriate amount of lordosis. It has been recognized that distraction of the vertebral bodies at either end of the defect is complicated, when the vertebral body replacement device is not adjustable. The aforementioned devices used to restore the size and shape of the vertebral body and adjacent discs removed by corpectomy are directed at fusion and do not provide for flexibility, compressibility and/or tilting for motion preservation of the intact adjacent vertebrae or stress-breaking and load-bearing features within the portion of the devices that stabilize the anterior column of the spine. Additionally, most existing height adjustable inter-body fusion corpectomy devices are deficient in their ability to selectively and incrementally adjust the opposing individual vertebrae to their proper height. This may result in over-distraction of one of the vertebra when using the existing adjustable corpectomy devices.

SUMMARY OF INVENTION

The present invention overcomes the disadvantages represented by the prior art by not requiring drilling procedures for threaded engagement of adjacent vertebrae and subsequent end plate preservation. It restores and preserves the disc intervertebral space with the proper curvature of the spine and functionality of the adjacent vertebra. As taught by this invention, the system and devices for insertion following disc removal requires no specialized surgical technique and allows for precise placement of the device and subsequent re-establishment of the proper inter-vertebral space and lordosis or kyphosis by either an anterior, anterior lateral, lateral, posterior lateral, or posterior surgical approach. Further, this invention permits precise implant size to fit within the space allowed and not endanger or damage adjacent structures due to over-distraction of the adjacent vertebra. Hence, incorrect implant size selection and the need for a variety of implant sizes is eliminated. An added advantage is, if removal is necessary, it would not result in iatrogenic destruction of the adjacent vertebrae. Also, spinal stability is obtained without the use of deep threads since such threads may adversely affect the vertebrae themselves.

The present invention is an inter-space artificial disc implant utilized to replace a damaged disc following discectomy. The present invention is also an adjustable corpectomy vertebral body replacement implant system that comprises of a rigid adjustable inter-space artificial vertebral body and adjacent artificial discs (which may be of different configurations) to replace a damaged vertebral body and adjacent artificial discs following corpectomy. The present invention is clearly an improvement over the prior art providing an implant prosthesis system intrinsically participating in this fusion process, self-stabilizing to the spinal segments, consistent with conventional methods of discectomy and corpectomy and uniquely and novel in its preservation of the integrity of the adjacent vertebrae and their functionality by providing flexibility, compressibility and/or tilting for motion preservation.

The present invention comprises an artificial disc implant for the purpose of which is to aid in and directly cause bone fusion at the bearing endplate surface portions of said device following the removal of a damaged disc. An alternate embodiment of the present invention comprises at least one rigid adjustable artificial vertebral intermediate body with attached artificial disc devices for the purpose of aiding and directly causing bone fusion at the bearing end plates surface portions of said devices following the removal of a damaged vertebral body and adjacent discs. Said prostheses are biocompatible, structurally load bearing devices, stronger than bone, capable of withstanding the forces generated within the spinal inter-space. The bearing endplate surfaces of the artificial disc devices may have a plurality of openings of specific size which can be filled with fusion promoting substances for inducing bone in-growth and osseous integration with the adjacent vertebrae, thereby forming a bony bond to the implants and each other. The implant bone-contacting surface may be textured, specifically designed, or otherwise treated by any known technology to enhance and achieve bone in-growth and fusion to the implant's end plates thereby enhancing stability of the artificial discs and/or corpectomy implant and to expedite fusion. The improved devices are configured and designed so as to promote their own stability within the vertebral inter-space following discectomy or the enlarged vertebral inter-space following corpectomy, to resist dislodgment, prevent micro-motion and stabilize and provide flexibility, compressibility, and/or tilting for motion preservation to the adjacent vertebrae.

The present implant is made of biocompatible materials, and in part bioresorbable materials, and has means if desired for increasing osseous integration, controlling hemostasis, preventing infection, treating tumors, and controlling pain. It establishes proper spinal height, support, curvature (lordosis and kyphosis) and capable of reducing vertebral listness (a forward or backward translation of one vertebra upon another as well as lateral misalignment of said vertebrae). It gives increased safety and precision which provides complete and easy visualization of the structures involved and adjacent vital structures (e.g. organs, neural structures and blood vessels and related bony surfaces). It also eliminates the need for a second surgical procedure to harvest bone. It also provides the system and material that is bio-resorbable and bio-compatible for additional means of stabilization to be used in conjunction with the implant artificial disc prosthesis or corpectomy implant for certain conditions that require additional stabilization for osseous integration. It may be used in distraction osteogenesis procedures in order to increase bone length and/or for inducing bone growth and osseous integration of the implant, and for controlling hemostasis and pain and preventing infection during and following the surgical procedure allowing for an increased opportunity of success.

Procedure for Implant

A conventional discectomy is performed and the vertebral end plates are roughened in preparation for use of the implant prosthesis of the present invention.

In an anterior cervical device (artificial disc or corpectomy vertebral body replacement) implantation, a short transverse incision is made across the front of the neck and off-center, preferably to the right of the midline and directly over the diseased or otherwise disc being replaced. The platysma muscle is dissected and split and the sternocleido-mastoid muscle with the carotid sheath is protected and retracted laterally. The esophagus, trachea and associated midline structures are protected and retracted medially, thus exposing the anterior aspect of the cervical spine. The disc involved is identified and removed by known, acceptable and conventional surgical methods. The adjacent vertebral end plates are gently scraped free of any remaining cartilage until diffuse fine punctuate decortication is achieved by the use of chisels, ronguer forceps, drills, saws, bone punches and scalpel that may be driven by air, electrically or ultrasonically as known to those skilled in the art. The dimensions of the inter-space are then measured in mild distraction and compared with the stereo-tactic pre-surgical x-ray diagnostic procedures and video imaging devices which helps to determine the exact intra-discal space to be restored relative to the vertebrae involved and the undamaged disc space that exists inferiorly and superiorly to the vertebrae involved. Following corpectomy, the measurement is determined for the enlarged intervertebral space to be restored relative to the adjacent vertebrae. The appropriate device or devices are selected for insertion with a specially designed device that establishes the necessary space for insertion behind the anterior lips of the vertebrae. The specially designed device is activated for establishing the desired inter-vertebral space or enlarged inter-vertebral space and said device is locked at the desired height. The implant is inserted and selectively and incrementally adjusted so as to maintain the desired inter-vertebral space following discectomy or the desired enlarged inter-vertebral space following corpectomy, with the end plates of the artificial discs in contact with the intact adjacent vertebral end plates. Alternatively, the prosthesis may consist of a single, double or multiple activated device so as to properly provide stability and the proper curvature or lordosis/kyphosis of the spine. Harvested bone or bone fill material commonly employed is packed into and around the implant. Alternatively, a new bone fill material is provided that is capable of being polymerized into a desired shape and size via being a bio-resorbable and biocompatible, photo-initiated, polymer and cured via visible light. In certain situations of trauma and disease following discectomy or corpectomy, additional stabilization is required and a bio-resorbable biocompatible photo-initiated polymer rod or plate and screws may be utilized and attached to the corpectomy vertebral body replacement implant as well as healthy vertebrae above and below the damaged site. Guide plates are provided for drilling holes to affix the plate and/or rods to the vertebrae with the necessary screws. Such screws may be bone screws or pedicle screws as known to those skilled in the art. In extreme cases, the additional stabilization may employ currently available rigid devices for such purposes with screws that are compliant or non-compliant. All areas are inspected and the wound is then closed in the routine manner. A further biocompatible, bio-resorbable, photo-initiated polymer is provided to enhance osseous integration, control hemostasis, control pain, and provide anti-microbial factors to prevent infection as well as anti-tumor factors. The devices may be used in the cervical, thoracic, and lumbar areas of the spine, utilizing anterior, anterior lateral, lateral, posterior lateral, posterior or any of the surgical approaches mentioned in combination as selected by the surgeon.

OBJECTS OF THE INVENTION

It is the object of the present invention to provide for an implant system in achieving functional restoration of the interverbral space, stabilization, fusion and motion preservation within a single procedure by a means consistent with the conventional method of discectomy or corpectomy and re-establishing the ideal and normal inter-vertebral space in terms of height, support, stability of the spine, normal curvature (lordosis or kyphosis) and motion preservation.

It is the object of the present invention to selectively and incrementally adjust the opposing individual vertebrae to their proper height. This prevents over-distraction of one of the opposing vertebra in restoration of the intervetebral space following corpectomy.

It is another object of the present invention to provide for a means of achieving an inter-space fusion of the artificial disc implant or the corpectomy vertebral body replacement implant endplate bearing surfaces and stabilization that is easier, quicker, safer and entails less blood loss than other known means.

It is another object of the present invention to provide for a means of achieving a one stage inter-space fusion stabilization and functionality with minimal damage and less removal of bone from the surface of the adjacent vertebrae than other known means.

It is another object of the present invention to provide for a device and system for inter-vertebral arthrodesis and stabilization and establishing the normal and pre-exiting inter-vertebral space in an easy, quick, safe and precise manner and in addition the entire procedure is performed under direct vision and may be further guided by optical imaging computerized devices or robotics.

It is another object of the present invention to provide for a device and system of inter-vertebral arthrodesis and stabilization and functionality that allows for the inter-vertebral space to be incrementally adjusted and is of variable sizes unlike any other known means and with greater simplicity and accuracy than any other known means.

It is another object of the present invention to provide for a modular prosthesis system having similar and multiple attachments or columns that allows for insertion through a small opening and then to reconstitute an inter-space occupying device much larger than would be normally inserted.

It is another object of the present invention to provide for a device and system that precisely fits the contours of any inter-space without the need to sacrifice any vertebral bone to accommodate the prosthesis and can be inserted from an anterior, anterior lateral, lateral, posterior lateral, or posterior surgical approach or any of the surgical approaches mentioned in combination as selected by the surgeon.

It is another object of the present invention to provide for a device and system with one, two or multiple adjustable artificial discs, having one end part of the rigid intermediate body and the other end fused with the intact adjacent vertebrae, that are interposed by bellows, with a bio-compatible, bio-resorbable rigid material surrounding or adjacent the bellows and making the bellows rigid until the resorbable rigid material is absorbed, after which the bellows become flexible, compressible and/or tiltable so as to act as a cushion for the artificial discs. If desired, the space within or inside the bellows may be filled with an elastomeric polymer or spring(s) or a combination of polymer and spring.

It is another object of the present invention to provide for a device and system having a rigid intermediate member attached at either end to a flexible, compressible and/or tiltable artificial disc with endplates and having flexible, compressible and/or tiltable bellows interposed therebetween said endplates and intermediate member. Said bellows are surrounded by a collar of a rigid bio-resorbable and bio-compatible material that causes the artificial disc to act as a fusion device during the healing period for a maximum osseous-integration of the end plates and subsequently the rigid bio-resorbable and bio-compatible collar resorbs thereby allowing the interposed bellows to flex, compress and/or tilt between the intact adjacent fused vertebra and the attached rigid vertebral intermediate body thereby providing motion preservation to the fused intact adjacent vertebra.

It is another object of the present invention to provide for a device and system having a rigid intermediate member attached at both ends to a flexible, compressible and/or tiltable artificial disc with upper and lower plate members and an intermediate flexible disc core interposed therebetween. The flexible, compressible and/or tiltable disc core maybe made of a bio-compatible and compressible material with a rigid collar of bio-compatible and bio-resorbable material surrounding or adjacent the flexible disc core, thereby making them rigid in order to enhance osseous-integration of the upper and lower plate members with the bones of the intact adjacent vertebrae. The upper and lower plate members are spaced from the rigid collar surrounding or adjacent the interposed disc core so as to allow limited tilting of the upper and lower plate members with respect to each other. Subsequently, the rigid collar will be resorbed and thereafter the flexible disc core will function in a flexible manner between the intact adjacent fused vertebrae and the attached rigid vertebral intermediate body thereby providing motion preservation to the fused site. Also, the rigid bio-compatible, bio-resorbable collar may act as a tissue barrier membrane so as to prevent in-growth of tissue during the healing phase following surgical implantation of the device that may adversely affect the performance of said device.

It is another object of the present invention to provide for a device and system with adjustable fusion devices having endplates that are affixed to the inter-space artificial vertebral body and adjacent vertebral endplates. Said inter-space artificial vertebral body is mounted between the adjustable fusion devices. Said fusion devices may be filled with bone stimulating factors once the desired intervertebral height between the intact adjacent vertebrae is attained, so as to promote osseous integration of the device and system with the intact adjacent vertebrae thereby resulting in fusion of said site. A bellows like assembly bisects the inter-space artificial vertebral body and a bio-compatible, bio-resorbable rigid material surrounds or adjacents the bellows and makes the bellows rigid until the resorbable rigid material is absorbed, after which the bellows become flexible, compressible and/or tiltable, allowing for motion preservation. If desired, the space inside or within the bellows may be filled with an elastomeric polymer, or spring(s) or a combination of polymer and spring.

It is another object of the present invention to provide for a device and system with artificial discs that has means for osseous integration with the adjacent vertebrae and said device having additional means to act as a shock absorber when heavy forces are exerted upon said device.

It is another object of the present invention to provide for a device and system that promotes fusion and reestablishes the normal height, support, stability, motion preservation and normal lordosis or kyphosis of the spine in a simple and precise manner.

It is another object of the present invention to provide a system with a biocompatible material for inducing bone growth that is easier to use than any other known materials for this purpose and can readily be shaped into a desired form and resist dislodgment. This material may also act over a prolonged period of time by being time released for this purpose.

It is another object of the present invention to provide a system for a biocompatible and bio-resorbable material for use in controlling hemostasis thereby enhancing the opportunity of success for osseous integration in individuals with abnormal clotting times. The hemostatic agent may also act over a prolonged period of time to further control post-operative bleeding, especially in individuals with poor clotting times, by being time released for this purpose.

It is another object of the present invention to provide a material and system for controlling post-operative pain following the discectomy or corpectomy surgical procedure, and said material may be time released locally over a period of time for this purpose.

It is another object of the present invention to provide a material having anti-microbial factors and system for preventing and controlling infection following the discectomy or corpectomy surgical procedure and said material may be time released locally and/or in combination with systemic drugs for this purpose.

It is another object of the present invention to provide a material and system for use of time released anti-tumor drugs or radiation seeds that may control or eradicate tumors related to the area of uses of said invention.

It is another object of the present invention to provide a device and system for use in distraction osteogenesis procedures unlike any other known devices and system currently employed.

These and other objects of the present invention will be apparent from the review of the following documentation and accompanying drawings.

BRIEF DESCRIPTION OF THE DRAWINGS

Although the invention has been described with regard to the preferred embodiments, it is recognized that other embodiments of the present invention may be devised which would not depart from the scope of the present invention.

FIG. 5 is an exploded perspective view showing a modification of the prosthesis of the present invention.

FIGS. 12A through 12I are several views of another modification of the present invention.

FIGS. 30A-D show the upper or lower section of the artificial disc of FIGS. 29A-B.

DESCRIPTION

Several embodiments of the present invention may be identified in whole or in part as a vertebral replacement implant, in particular, the rigid adjustable corpectomy vertebral body replacement implant system of the present invention. For example, the embodiments shown in FIGS. 1, 2, 3, 4, 5, 6, 7, 8A-8B, 9, 10A-10C, 11A-11D, 13A-13D, 16, and 17A-17C.

Figure 1:
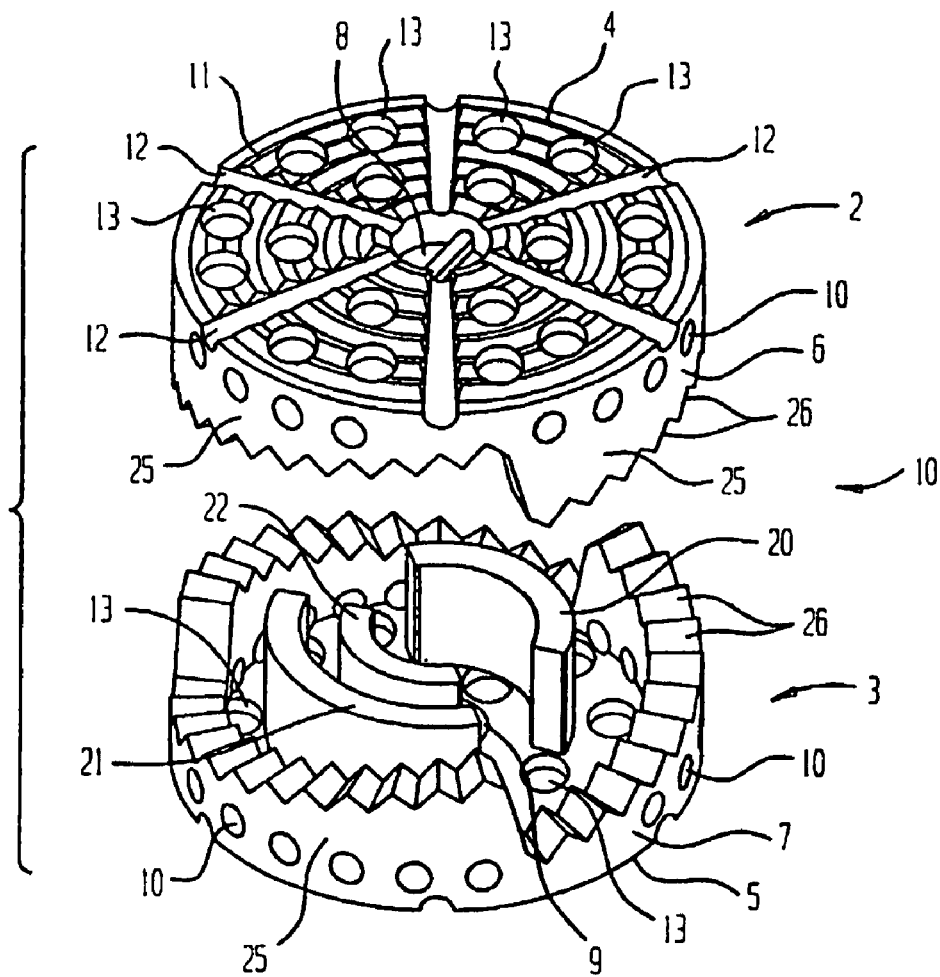
FIG. 1 is an exploded perspective view showing a prosthesis made in accordance with the present invention.
Figure 4:
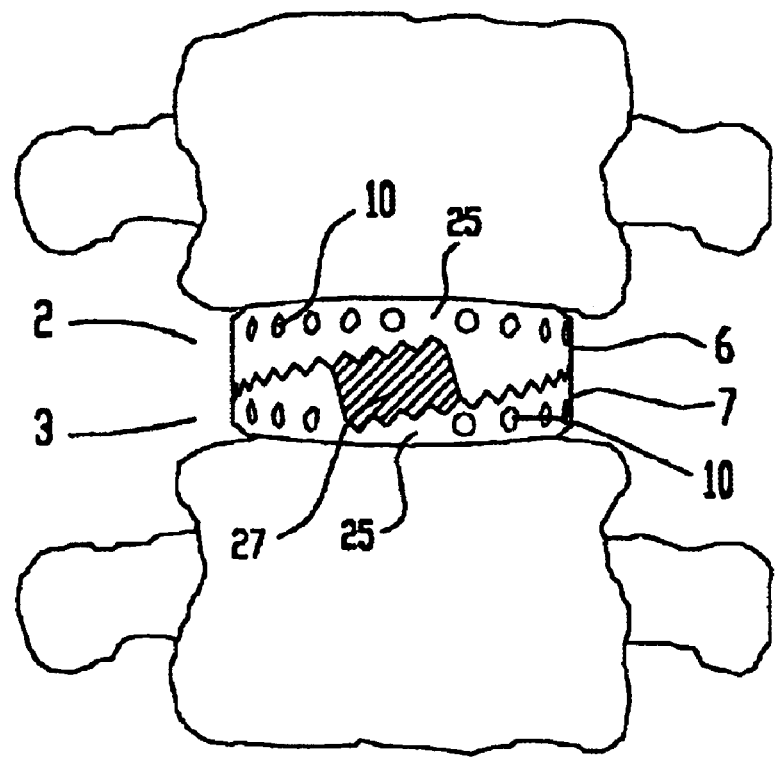
FIG. 4 is a rear view of the prosthesis as shown in FIG. 3.

Referring to the drawings, and particularly to the embodiment of the invention shown in FIGS. 1 and 4, the prosthesis or implant of the present invention comprises a cage 1 having a pair of upper and lower sections 2 and 3 which are identical to and complimentary to each other and are adapted to interfit and rotate relative to each other. The upper section 2 has a top bearing surface 4 and the lower section 3 has a bottom bearing surface 5 which is substantially identical to the top bearing surface 4. The bearing surfaces 4 and 5 are shown as being circular and have circular side-walls 6 and 7, respectively, extending at right angles from each. The top and bottom bearing surfaces 4 and 5 have a central opening 8 and 9, respectively, and the side walls 6 and 7 have a plurality of openings 10 therein. Circular ridges 11 are provided on the top and bottom bearing surfaces 4 and 5, each of which are concentrically located with respect to the central openings 8 and 9. Radiating outwardly from each central opening 8 and 9 are channels 12. A plurality of openings 13 are preferably provided in the top and bottom bearing surfaces 4 and 5. Bearing surfaces 4 and 5 are not limited to being circular in shape as shown and can be oval or having the shape of the vertebrae endplates or other shapes. Similarly, ridges 11 are not limited to being concentrically circular as shown and other shapes or non-uniformly aligned ridges may be used.

Spaced inwardly from the side walls 6 of each of the two sections 2 and 3 are a pair of opposed curved outer guide partitions 20 and 21, each of which is substantially equally spaced from the central openings 8 and 9 and equally spaced from their respective side walls 6 and 7. Each of the top and bottom sections 2 and 3 have an inner curved guide partition 22 inwardly spaced from one of the outer partitions 20 and 21. The top and bottom sections 2 and 3 are adapted to be assembled together so that the partition 20 of one section will fit between the partitions 21 and 22 of the other section, as more clearly shown in FIG. 2. This will permit the two sections 2 and 3 to rotate relative to each other while remaining in axial alignment with each other. Furthermore, the partitions 20, 21 and 22 limit the degree of rotation when partitions 20, 21 or 22 of the top section 2 is rotated until it comes in contact with the corresponding partitions 20, 22 or 21, respectively, of bottom section 3. A spring 41 is inserted in and extends between the openings 8 and 9 in order to hold the two section 2 and 3 together and biased towards each other. Other means of biasing, for example, elastic string or post can be used.

Figure 8A:
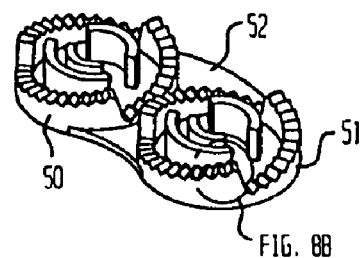
FIG. 8A is a perspective view of a part of the prosthesis shown in FIG. 7
Figure 8B:
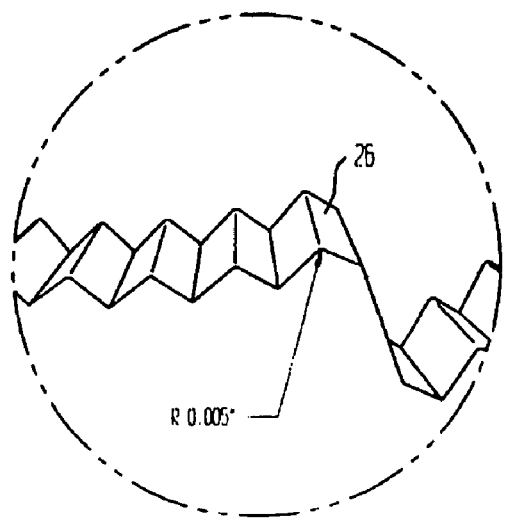
FIG. 8B is an extremely magnified detail of a portion thereof.

The side walls 6 and 7 of each section 2 and 3 are arranged in a plurality of inclined cam surfaces 25 which extend substantially from the bearing surfaces 4 and 5 of each and incline away from the bearing surfaces 4 and 5. In the embodiment shown in FIGS. 1 through 4, three identical cam surfaces 25 are shown on each section 2 and 3. However, it will be understood that the number of cam surfaces 25 may be increased or decreased if desired. The cam surfaces 25 of each section 2 and 3 are complimentary to each other. In the drawings, the edge of each cam surface 25 has a plurality of teeth 26. The teeth 26 and the cam surfaces 25 of each top and bottom section 2 and 3 are the same so that the teeth 26 of each will interfit with each other when the two sections 2 and 3 are assembled together. Preferably, the apexes of the teeth 26 are rounded with a radius of 0.005 inch as shown in FIG. 8B. However, different radii can be used. The sections 2 and 3 are adjusted to the desired height by rotating one section relative to the other. The cam surfaces 25 will move the sections 2 and 3 away from each other or toward each other and the teeth 26 in both sections will interfit with each other to prevent rotary displacement and to hold the sections 2 and 3 at the desired height. The openings 10 on the side walls 6 and 7 may be used to rotate one section relative to the other section by inserting a tool (not shown) therein and rotating one section relative to the other section.

Figure 3:
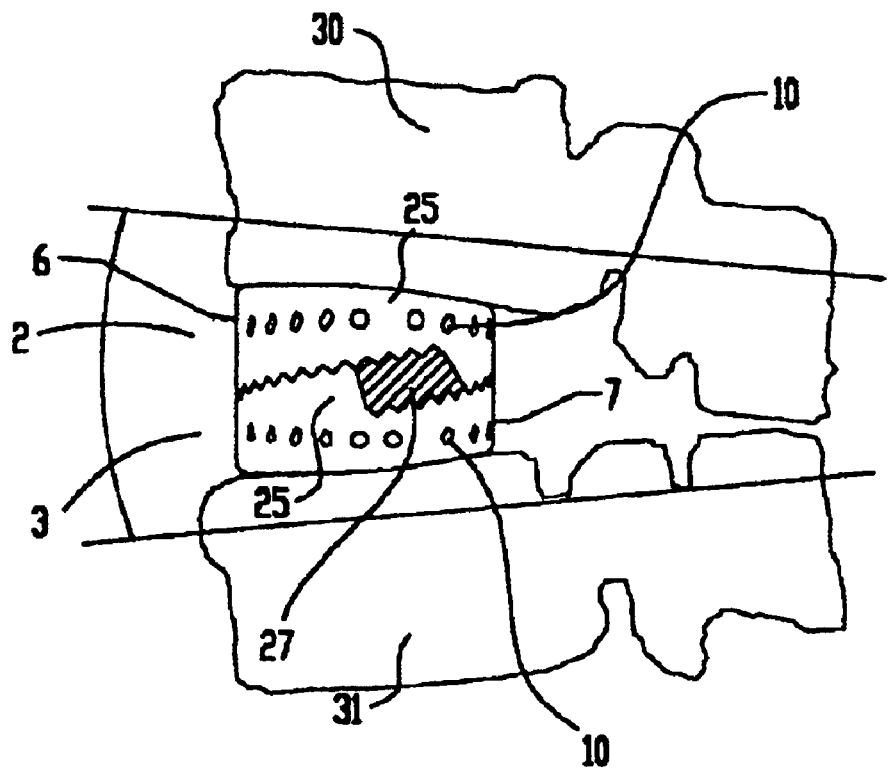
FIG. 3 is a highly simplified side view showing the prosthesis in place between vertebrae.

The two sections 2 and 3 of the cage 1 are assembled together and inserted between vertebrae 30, 31 as shown in FIGS. 3 and 4. Prior to insertion between vertebrae 30 and 31, various substance or agents 27 to promote osseous integration (e.g. De-Mineralized Bone Matrix available from Grafton Inc., which is putty-like in an uncured state for ease of placement and becomes not pliable upon curing), other various substances or agents may be utilized to control post-operative bleeding, pain, infection or control or eradicate tumors may be placed between the two sections 2 and 3 and/or between cage 1 and vertebrae 30 and 31. These substances or agents 27 may be incorporated in a bio-compatible or bio-resorbable material. The bio-compatible or bio-resorbable material containing the various substance or agents 27 may be photocurable polymers, by either ultraviolet light in the range of 350-385 nanometers in wavelength or visible light in the range of 385-550 nanometers in wavelength. Furthermore, the bio-compatible or bio-resorbable material may also be colored in the uncured state and turn clear upon curing to aid in assuring visually that the polymer has been completely cured, such as photo-initiator HU-470 available from Spectra Inc.

The vertebrae 30 and 31 and the space between them have been prepared (by cleaning and otherwise) to receive the cage 1 as described hereinabove. After the cage 1 is inserted between the two vertebrae 30 and 31, the two sections 2 and 3 are rotated relative to each other until their bearing surfaces 4 and 5 make the proper contact with the opposed bearing surfaces of the vertebrae 30 and 31 in order to support the vertebrae. The ridges 11 on the bearing surfaces 4 and 5 permit the two sections to be easily rotated on the vertebrae and permit positive contact with the vertebrae. The channels 12 act as a reservoir for cartilage and other bone material to enter as the bearing surfaces 4 and 5 grasp and become enmeshed with the two sections 2 and 3 thereby fusing the cage 1 between adjacent vertebrae 30 and 31. Channels 12 may also be coated with a bone initiating or stimulating material to further promote osseous integration.

Referring now to the embodiment shown FIG. 5, the two sections 2A and 3A of the cage 1A are similar to the sections 2 and 3 of cage 1 described in the embodiment of FIGS. 1 through 4. However, in this instance, four cam surfaces 25A are shown.

Figure 6:
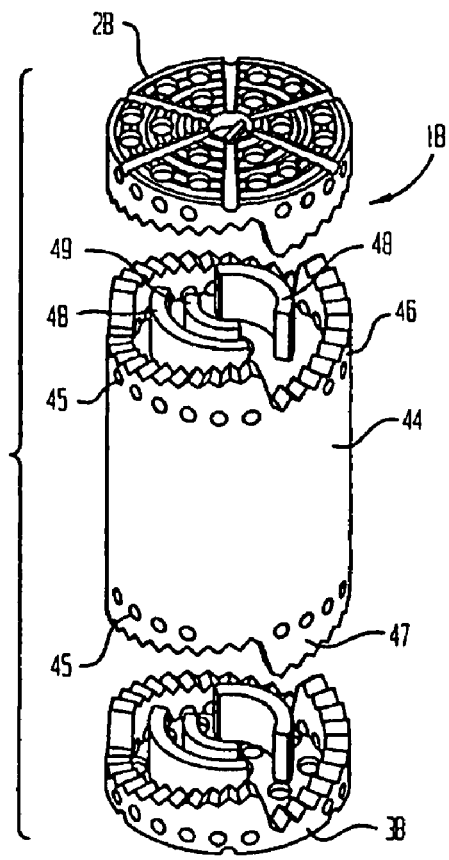
FIG. 6 is an exploded perspective view showing another modification of the present invention for vertebral replacement.

In the embodiment shown in FIG. 6, the top and bottom sections 2B and 3B of cage 1B are similar to the sections 2 and 3 discussed above representing an artificial disc. However, an elongated connecting tube 44 representing the removed diseased vertebral body is interposed between them. The top and bottom end edges of the connecting tube 44 has cam surfaces 46, teeth 47, partitions 48 and 49 and openings 45 and are similar to the cam surfaces 25, teeth 26, partitions 20 and 22 and openings 10 in the sections 2 and 3 of the FIGS. 1 through 4 embodiment. Hence, the sections 2B and 3B are complimentary to the end edges of the tube 44. With this structure, if the space between the vertebrae is very large, the connecting tube 44 is used in order to span the distance between the two sections 2B and 3B to fill the space between the vertebrae. The structure shown in FIG. 6 may be used to replace a vertebrae.

Figure 7:
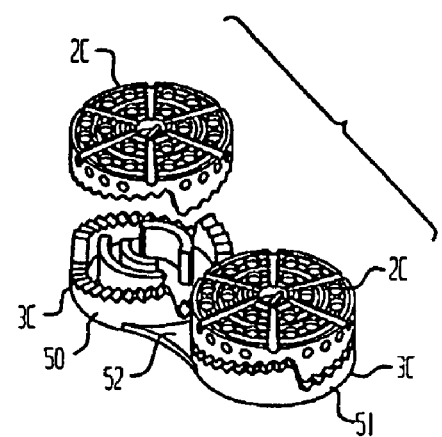
FIG. 7 shows another modification of the present invention for aligning the vertebrae.

Referring to the embodiment shown in FIGS. 7 through 8B the prosthesis shown comprises double cages 50 and 51 which has top sections 2C similar to the top section 2 of the FIGS. 1 through 4 embodiment. The bottom sections 3C are also the same but are connected together by a web 52. The top sections 2C are rotated relative to the bottom sections 3C. The cages 50 and 51 can be adjusted to different heights depending on the spinal curvature that is desired. Adjusting the cages to different heights will cause the cages to act as a leveling device.

Figure 9:
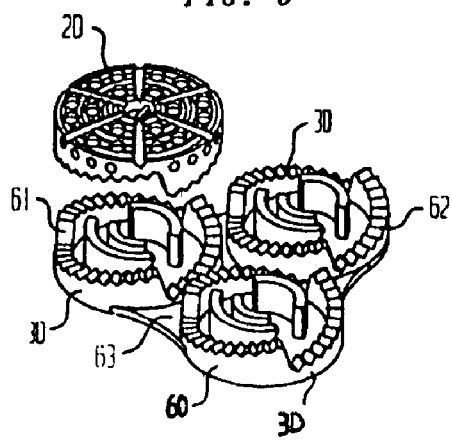
FIG. 9 is a perspective view showing another modification of the present invention for multi-directional leveling of the vertebrae.

The embodiment shown in FIG. 9 shows a prosthesis that is similar to the embodiment shown in FIGS. 7 through 8B. However, in this embodiment, three cages 60, 61 and 62 are used with the top sections 2D of each (only one is shown) being the same as the top section 2 of the FIGS. 1 through 4 embodiment and the bottom sections 3D being connected together by a web 63. Again, the cages 60, 61 and 62 can be individually adjusted to different heights to act as a leveling device that allows multi-directional flexibility without sacrificing stability and restores natural lordosis or kyphosis of the vertebrae.

Figure 10A:
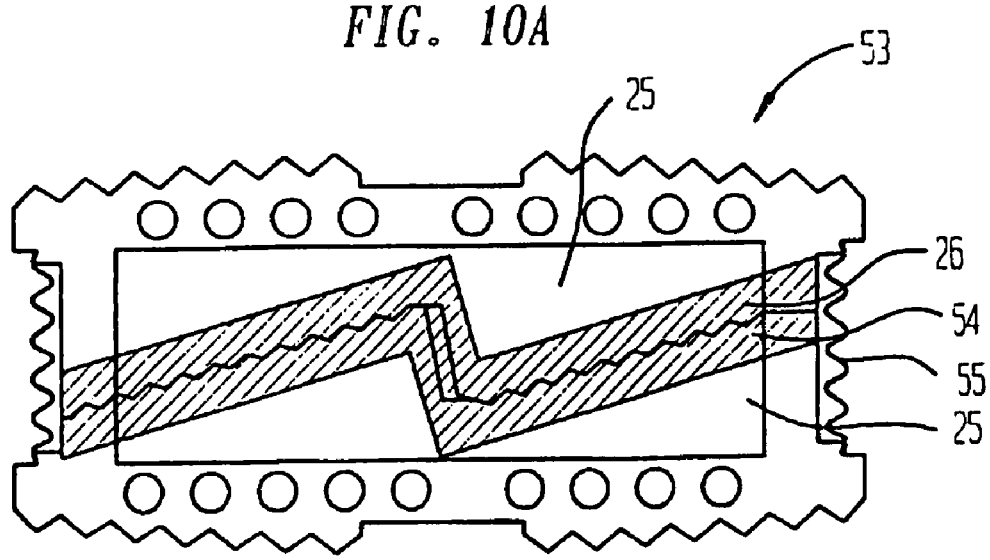
FIGS. 10A through 10C are several views of another embodiment of the present invention as a flexible prosthesis partially made of a bio-resorbable material.
Figure 10B:
Figure 10C:
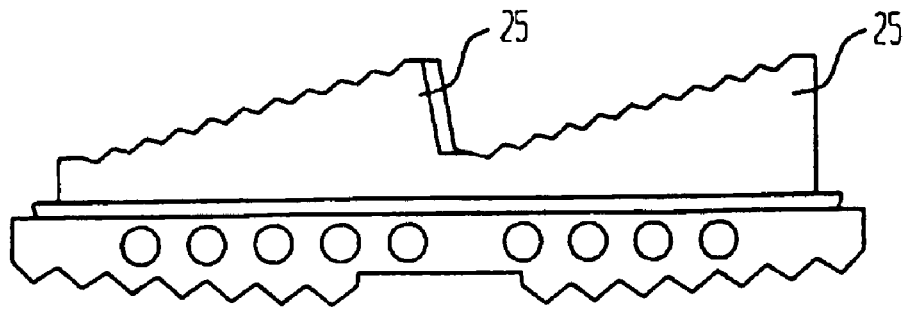

FIGS. 10A through 10C show another embodiment of the present invention. A cage 53 is similar to the cage described in connection to FIG. 1. However, the outer edge 54 of the cam surfaces 25 and the teeth 26 are made of a bio-resorbable material. A titanium bellows 55 surrounds the cage 53. The bio-resorbable material between the upper and lower sections of cage 53 will degrade eventually and leaving the bellows 55 to give the cage multi-directional flexibility, compressibility and tiltability without causing associated instability.

Figure 11A:
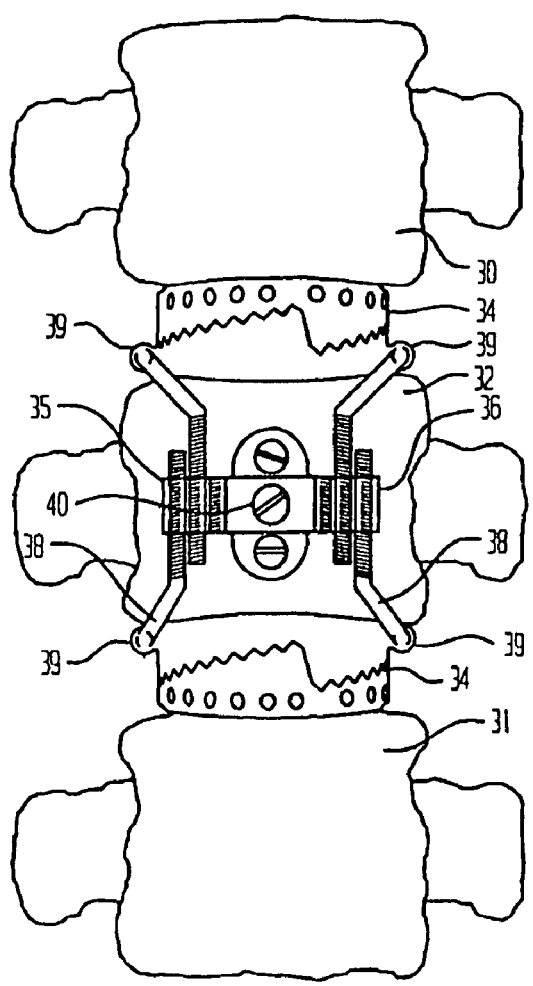
FIGS. 11A through 11D are several views of another embodiment of the present invention for two level stabilization of the vertebrae.
Figure 11B:
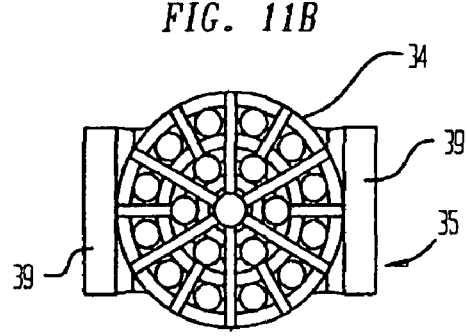
Figure 11C:
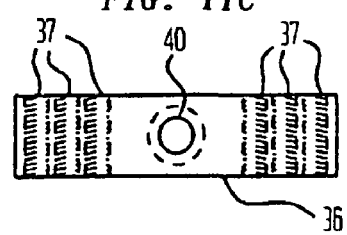
Figure 11D:
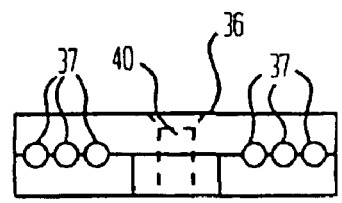
Figure 13A:
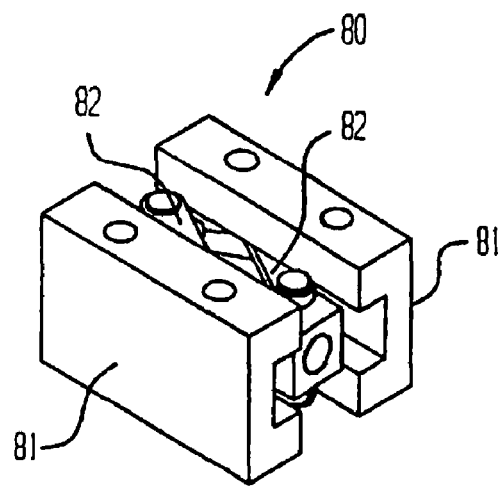
FIGS. 13A through 13D are several views of another modification of the present invention.
Figure 13B:
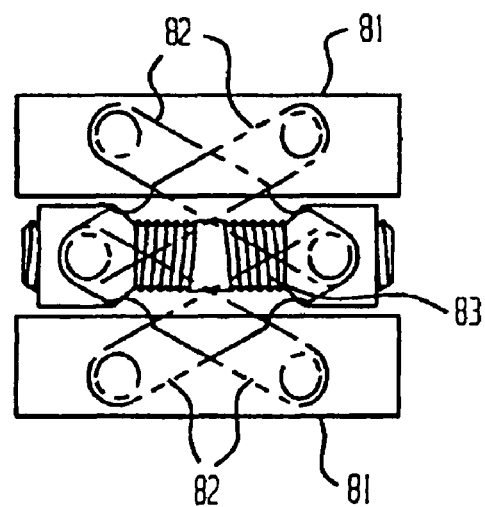
Figure 13C:
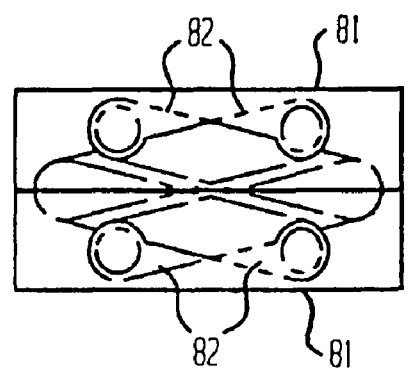
Figure 13D:
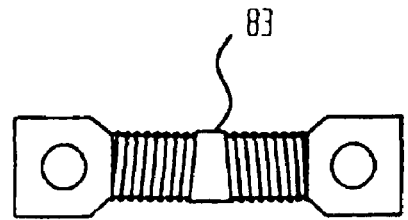

FIGS. 11A through 11D show another embodiment of the present invention. In this embodiment, an upper vertebrae, 30, a lower vertebrae 31, and an intermediate vertebrae 32, are to be linked together. A cage 34 similar to the cage described in connection with FIG. 1, is inserted between the upper vertebrae 30 and the intermediate vertebrae 32, and another similar cage 34 is inserted between the lower vertebrae 31 and the intermediate vertebrae 30. A connecting and stabilizing assembly 35 is provided to connect the two cages 34 and to connect and stabilize all the vertebrae 30, 31 and 32. The connecting assembly 35 comprises a clamping plate 36 having a plurality of threaded openings 37 therein. The clamping plate 36 is to be screwed or otherwise mounted to the central vertebrae 32 by a screw or some other suitable means 40. Connecting rods 38 are inserted through the openings 37 in the clamping plate 36. The outer ends of the connecting rods 38 have holding knobs 39 which bear against the outer surfaces of each cage 34 on each side thereof as shown in FIG. 11B. With this structure the clamping plate 31 is affixed to the intermediate vertebrae 32 and the holding knobs 39 of each connecting rod 38 extends along both sides of each of the cages 34 and stabilizes the cages and the vertebrae 30, 31 and 32.

Referring now to the embodiment in FIGS. 12A to 12I, a gear type expansion cage 70 is shown. The expansion cage 70 comprises a pair of curved elongated outer bearing surfaces 71 each of which have a geared threaded opening 72 therein. A gear wheel 73 has threaded extensions 74 on each side thereof which are inserted in the threaded openings 72 in each of the curved bearing surfaces 71. A pair of such gears 73 with threaded extensions 74 is mounted on each end of the bearing surfaces 71 and the two gears 73 are connected together by a central gear 75. When one of the gears 73 is rotated, that end of the bearing surface 71 will expand or contract depending on the direction that the gear 73 is turned and at the same time, the central gear wheel 75 will also rotate the second gear 73 in order to expand that side of the curved bearing surface 71. In this manner, the curved bearing surfaces 71 will move away or toward each other to fill the gap between the vertebrae. The outer surfaces of the bearing surfaces 71 have grooves 76 to permit and enhance fusing the prosthesis with bone.

Referring now to the embodiment shown in FIG. 13A through 13D, a jack-type cage 80 is shown. A pair of opposed bearing surfaces 81 (shown elongated and flat—but which may be curved) are connected together by a plurality of cross arms 82 through the intermediation of a jack screw 83. The ends of the arms 82 are connected to each end of the two bearing surfaces 81 and to each end of the jack screw 83. Rotating the jack-screw 83 in one direction or the other extends or contracts the arms 82 in either one direction or the other to either move the bearing surfaces 81 away from each other or to move them toward each other. In this manner, the bearing surfaces 81 will fill the gap between vertebrae.

Figure 14A:
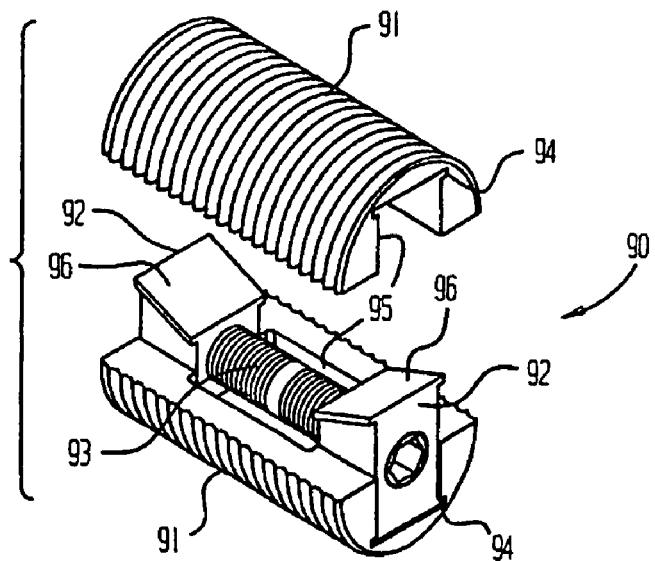
FIGS. 14A through 14C are several views showing another modification of the present invention.
Figure 14B:
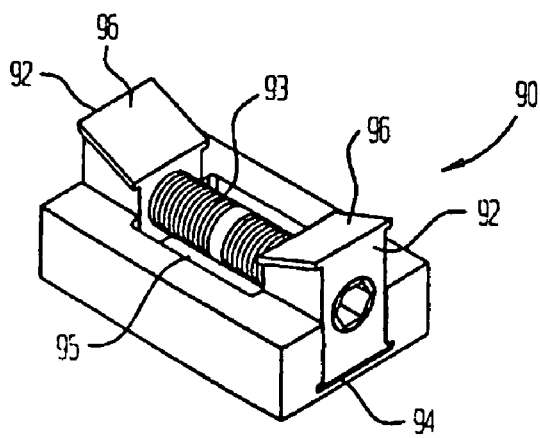
Figure 14C:
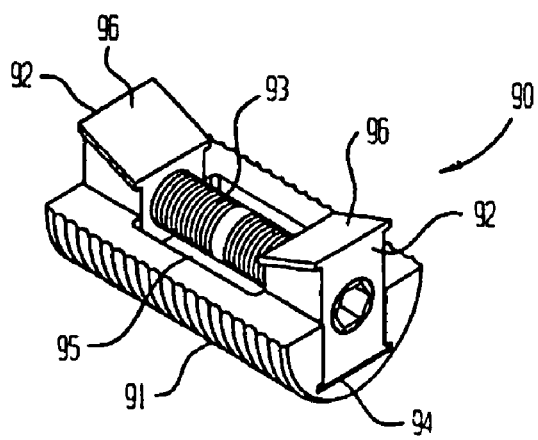

In the embodiment shown in FIGS. 14A through 14C, a wedge type cage 90 is described. The curved elongated outer bearing surfaces 91 have a pair of wedges 92 therebetween which are controlled and connected together by a screw 93. The wedges 92 are adapted to move in grooves 94 in the inner channels 95 in the bearing surfaces 91. The wedges 92 having opposed inclined surfaces 96. By rotating the screw 93 in one direction or the other the wedges 92 are moved closer or further apart from each other and since the surfaces 96 are angled in opposite directions, the two bearing surfaces 91 are moved towards or away from each other. In this manner, the space between the vertebrae may be filled by merely adjusting the height of the two bearing surfaces 91, as described above.

Figure 15A:
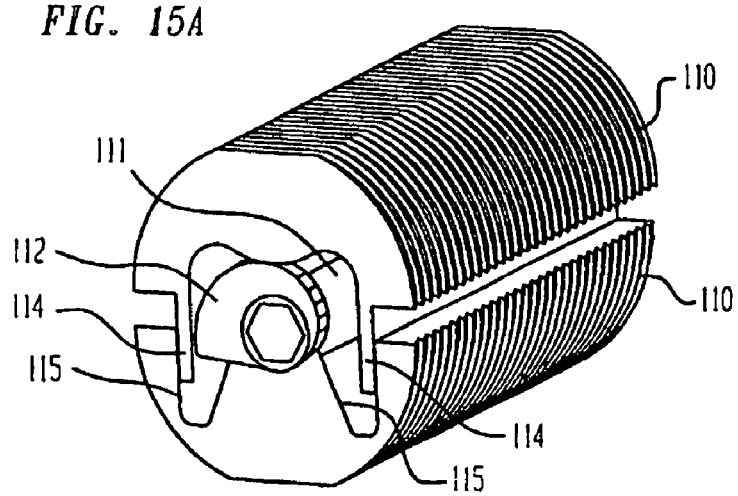
FIG. 15A through 15C are several views showing another modification of the present invention.
Figure 15B:
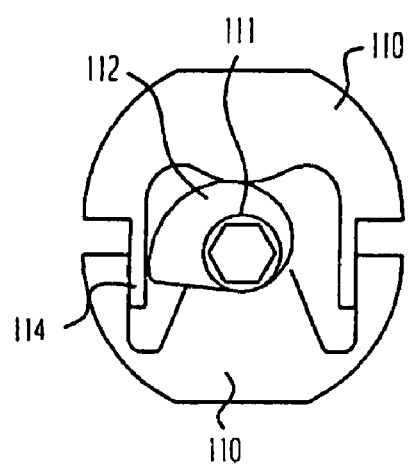
Figure 15C:
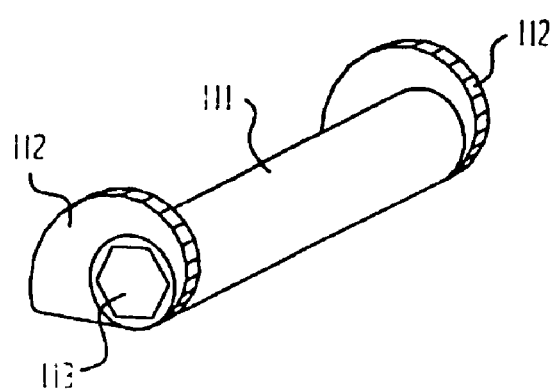

FIGS. 15A through 15C show a cam type expandable cage. In this embodiment, the opposed curved elongated bearing surfaces 110 have a rod 111 interposed between them with cams 112 in each end. The rod 111 has an opening 113 at its edges which permit the rod 111 and the cams 112 to be rotated. When the rod 111 is rotated, the cams 112 will rotate and strike the interior of the two bearing surfaces 110 to move the two bearing surfaces 110 towards or away from each other. A pair of elongated guides 114 extend from the interior of one of the bearing surfaces 110, which correspond to a pair of grooves 115 on the interior of the opposite bearing surface 110, to prevent lateral movement and dislodgment of the opposed bearing surfaces 110 from each other.

Figure 16:
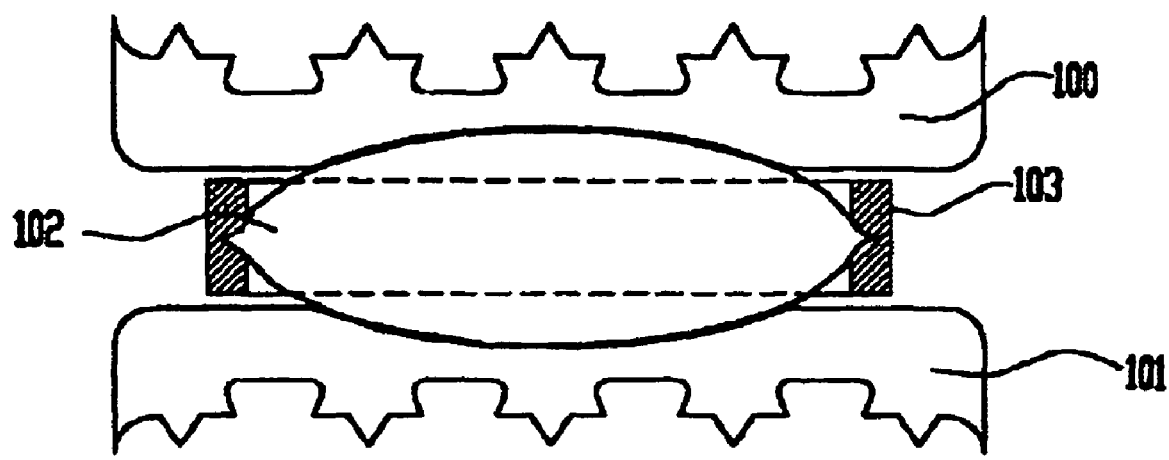
FIG. 16 shows another modification of the present invention.

Referring to the embodiment of FIG. 16, a flexible spinal fusion prosthesis is shown in which upper and lower plate members 100 and 101 are provided with an intermediate convex flexible disc 102 interposed therebetween. The disk 102 may be made of titanium or some other known material which is biocompatible and compressible. A rigid collar 103 of resorbable material surrounds the disc 102 to make the flexible disc 102 rigid in order to allow integration of the upper and lower plate members 100 and 101 with the bones of the vertebrae. The collar 103 will be resorbed and thereafter the flexible disc 102 will function in a flexible manner between the vertebrae.

Figure 2:
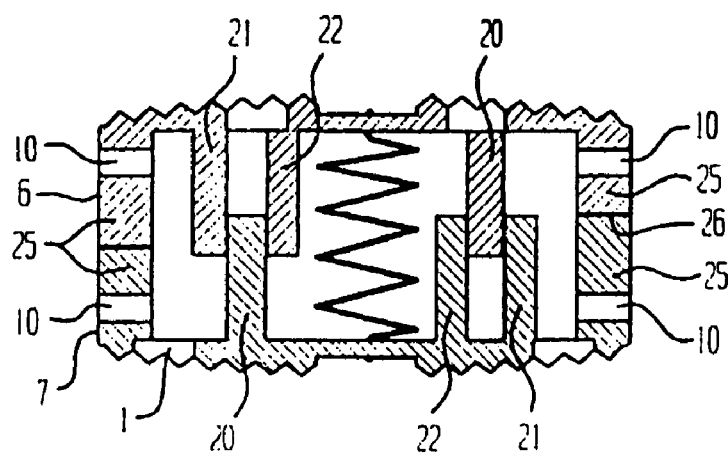
FIG. 2 is a cross-sectional view of the prosthesis, with a spring biasing the top and bottom sections.
Figure 17A:
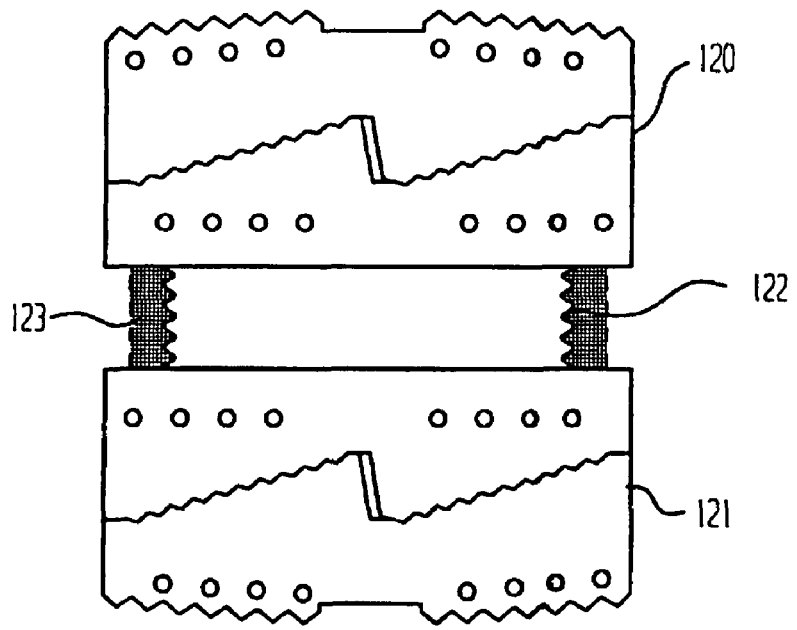
FIGS. 17A through 17C are several views showing another modification of the present invention.
Figure 17B:
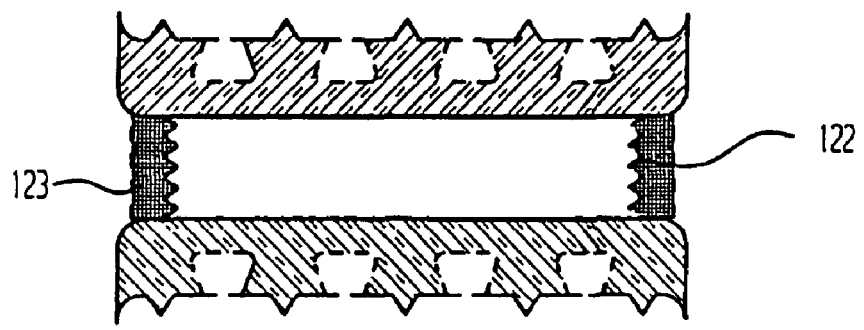
Figure 17C:
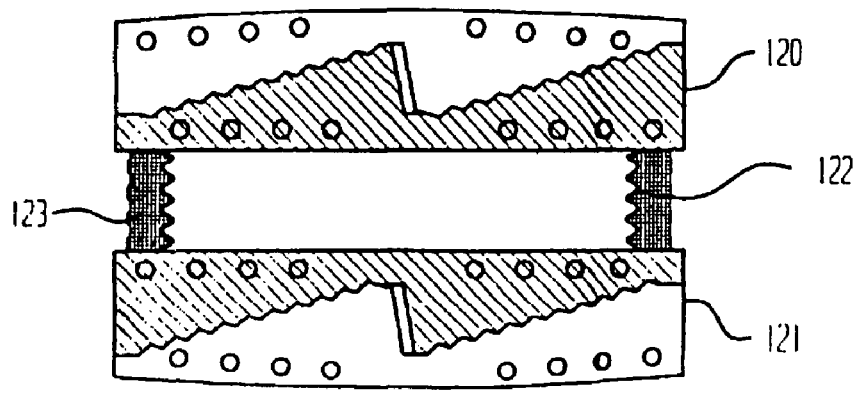
Figure 18A:
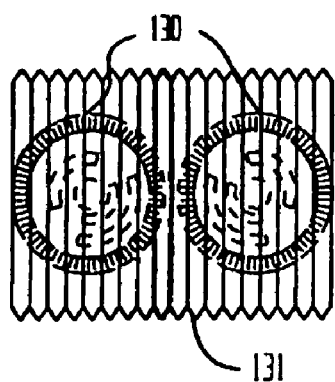
FIGS. 18A through 18G are several views showing another modification of the present invention.
Figure 18B:
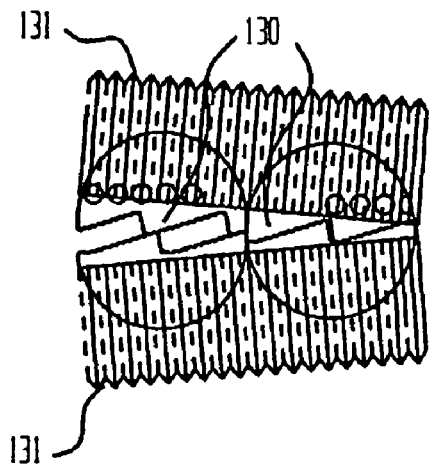
Figure 18C:
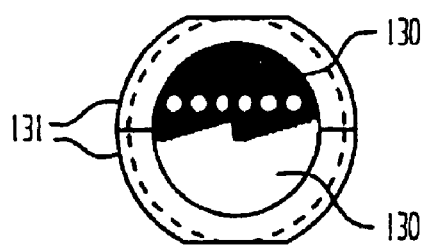
Figure 18D:
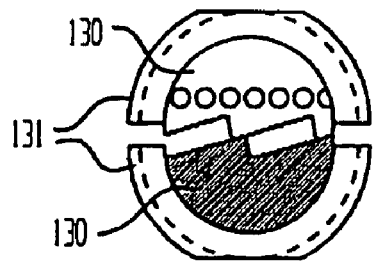
Figure 18E:
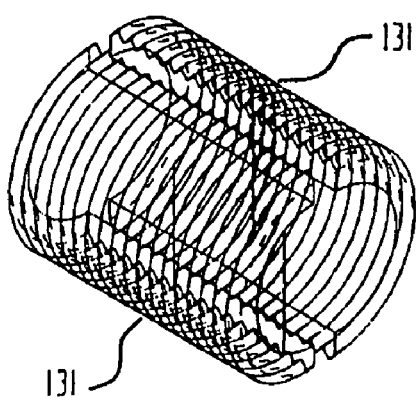
Figure 18F:
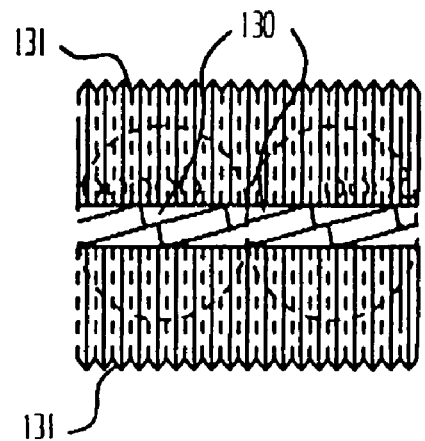
Figure 18G:
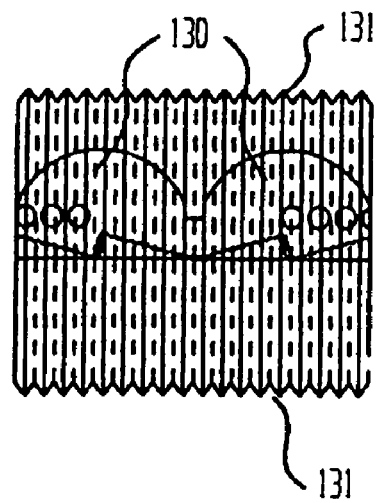

With respect to the embodiment shown in FIG. 17A to 17C, a pair of expandable cages 120 and 121 similar to the cages of FIGS. 1 and 2 are mounted between vertebrae in a spaced relationship to each other. A titanium bellows-like assembly 122 is interposed between the spaced cages 120 and 121. Resorbable rigid material 123 surrounds the bellows 122 and make the bellows 122 rigid until the resorbable rigid material 123 is absorbed, after which the bellows 122 will become flexible to act as a cushion between the two cages 120 and 121. If desired the space between the bellows 122 may be filled with a polymer.

In the embodiment shown in FIGS. 18A to 18G, a plurality of expandable cages 130 similar to the cage 1 of FIGS. 1 through 4, are interposed between a pair of curved elongated bearing surfaces 131 so that contact with the vertebrae is made by the curved bearing surfaces 131 rather than by the expansion cages 130 themselves. The internal expansion cages 130 can be adjusted to different heights to permit the bearing surfaces 131 to achieve different heights and angles.

Figure 19:
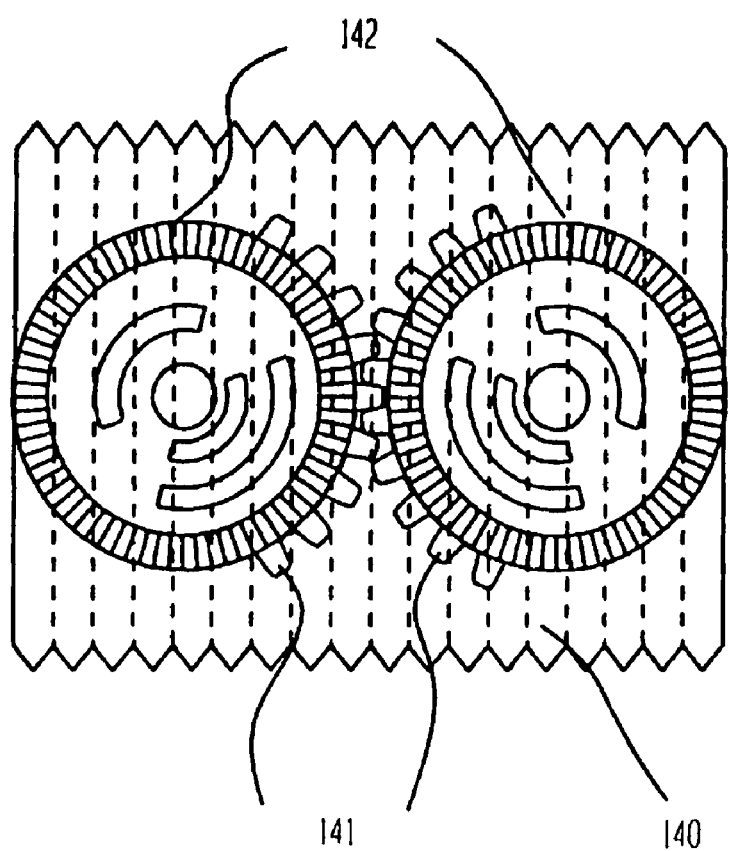
FIG. 19 shows still another modification of the present invention.
Figure 20A:
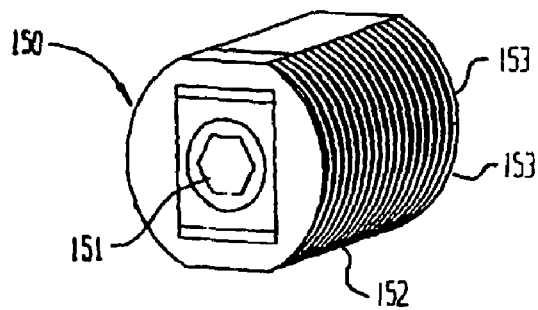
FIGS. 20A through 20F are several views showing still another modification of the present invention.
Figure 20B:
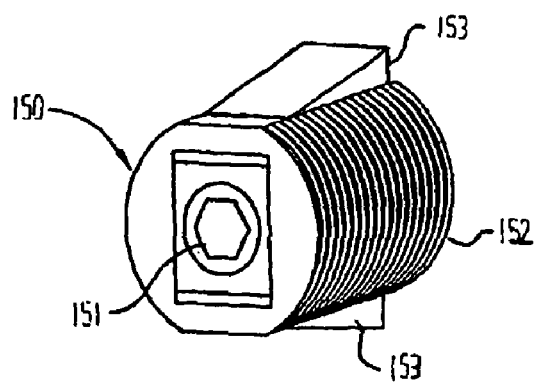
Figure 20C:
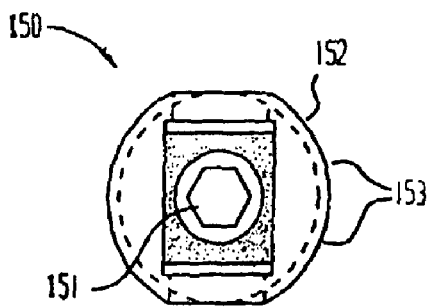
Figure 20D:
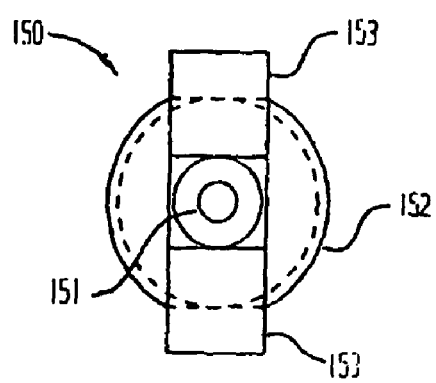
Figure 20E:
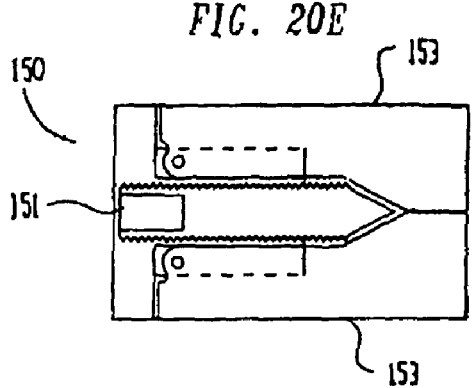
Figure 20F:
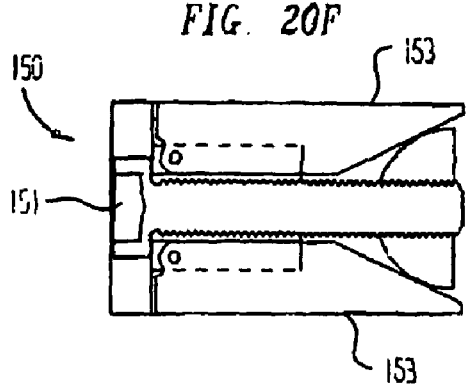

In the embodiment shown in FIG. 19 the elongated curved bearing surfaces 140 have a pair of cages 142 similar to the cage shown in FIG. 1. Each cage has an outer gear 141 extending from its outer surface. When the gears 141 are rotated in one direction, the bearing surfaces 140 are moved towards each other.

It will be noted that in FIG. 19 the two gears are the same size and ratio. However, it is within the purview of the present invention for the two gears to be of different ratios and sizes so that movement of one gear will expand its cage to a certain height, and the other cage, having a gear of a different ratio, will expand its cage to a different height. This may also be accomplished by a connecting gear between the two gears (not shown). It is also possible to accomplish the same purpose by having geared teeth of different heights so that the two geared cages may move to different expansions.

Referring to the embodiment shown in FIGS. 20A through 20F, a tapered expandable cage 150 is shown. An expansion screw 151 is mounted in the cage 150 having a circular solid front portion 152 and expandable curved rear bearing surfaces 153. By rotating the screw 151, the inner edge of the screw 151 will contact the expandable bearing surfaces 153 and expand them. In version A (FIG. 20E), the expandable screw 151 has a point 154 which moves toward the expandable bearing surfaces 153 and spreads them apart. In version B (FIG. 20F), the expansion screw 151 has a tapered blunt edge 155 which contacts the expandable bearing surfaces 153 and spreads them apart.

Figure 21:
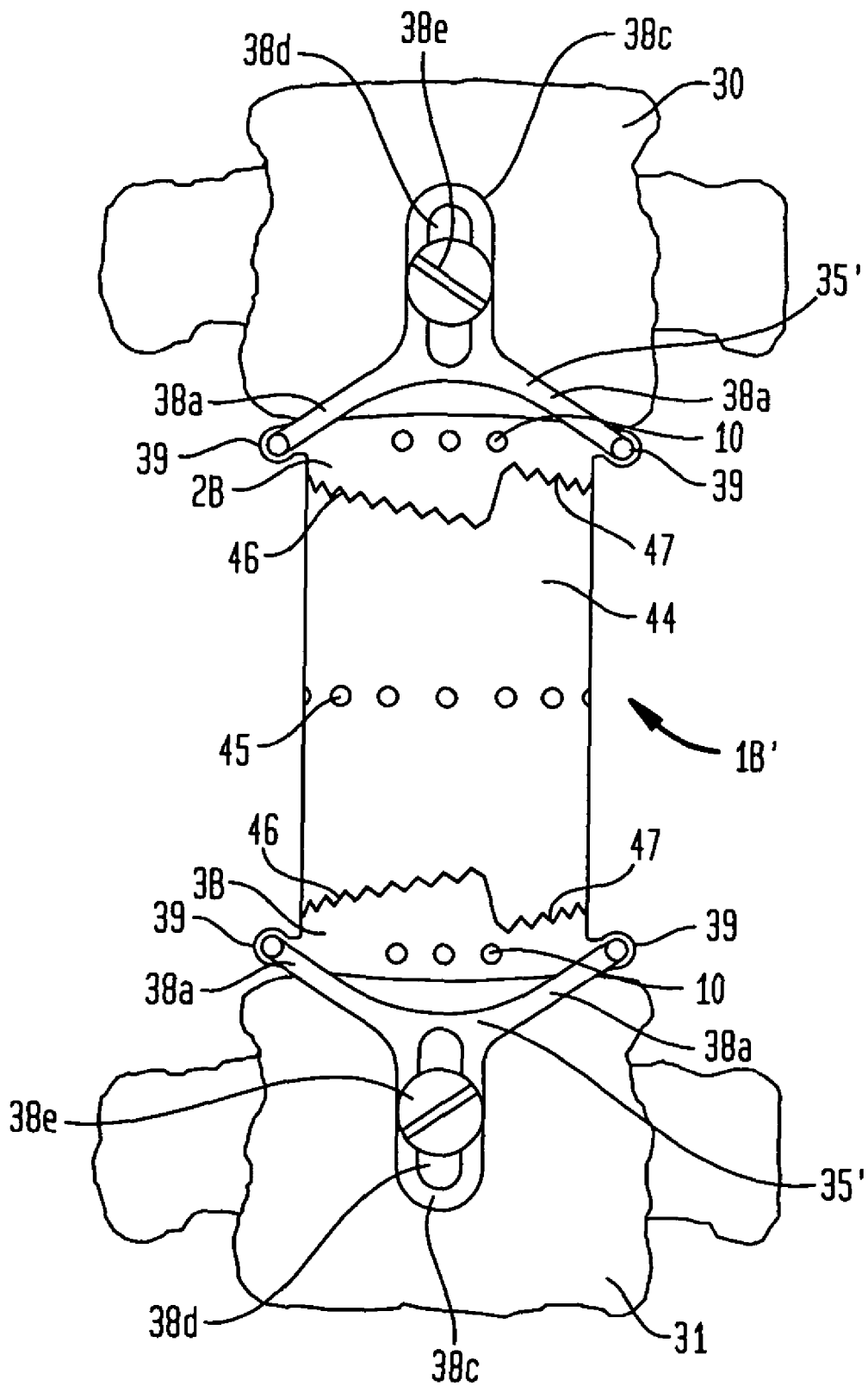
FIG. 21 shows the embodiment of FIG. 6 being used as a rigid adjustable vertebral replacement implant system that connects to and stabilizes adjacent vertebrae.

FIG. 21 shows the cage 1B of FIG. 6 being used as a vertebral replacement implant. Implant 1B' is connected to adjacent vertebrae 30 and 31 with a connecting and stabilizing assembly 35'. The function and purpose of the connecting and stabilizing assembly 35' is similar to the connecting and stabilizing assembly 35 of FIG. 11A. Similar to the connecting and stabilizing assembly 35 of FIG. 11A, the connecting and stabilizing assembly 35' comprises a pair of connecting rods 38a, with one end of each attached to a holding knob 39 which bears against the outer surfaces of the top and bottom sections 2B and 3B of implant 1B'. The two holding knobs 39 are shown to be on opposite sides of top and bottom sections 2B and 3B and parallel to each other, but they can be also located at different locations of the top and bottom sections 2B and 3B or have different configurations. The opposite ends of each pair of connecting rods 38a joined to form a tab 38c. Tab 38c contains a slot opening 38d for receiving a screw 38e or other suitable means for attaching the connecting and stabilizing assembly 35' to the vertebrae 30 or 31. The slot opening 38d allows fine-tune positioning of the connecting and stabilizing assembly 35' before securing it with screw 38e to the vertebrae 30 or 31. As a rigid adjustable vertebral intermediate body, implant 1B' is inserted between adjacent vertebrae as described in connection with cage 1 of FIG. 1, except that implant 1B' replaces a vertebral body and discs whereas cage 1 replaces a disc only. After insertion of implant 1B' between adjacent intact vertebrae 30 and 31, screw 38e securely fixes each connecting and stabilizing assembly 35' to the vertebrae 30 and 31. The height of implant 1B' is then adjusted to the desired height by rotating the connecting tube 44 relative to the top and bottom sections 2B and 3B, respectively. The cam surfaces 46 will move top and bottom sections 2B and 3B away from each other or toward each other and the teeth 47 will interfit with each other to prevent rotary displacement and hold the top and bottom sections 2B and 3B at the desired height. The openings 45 on the connecting tube 44, and the openings 10 on the top and bottom sections 2B and 3B, may be used to rotate connecting tube 44 relative to top and bottom sections 2B and 3B by inserting a tool (not shown) and turning connecting tube 44 relative to the top and bottom sections 2B and 3B.

Figure 22:
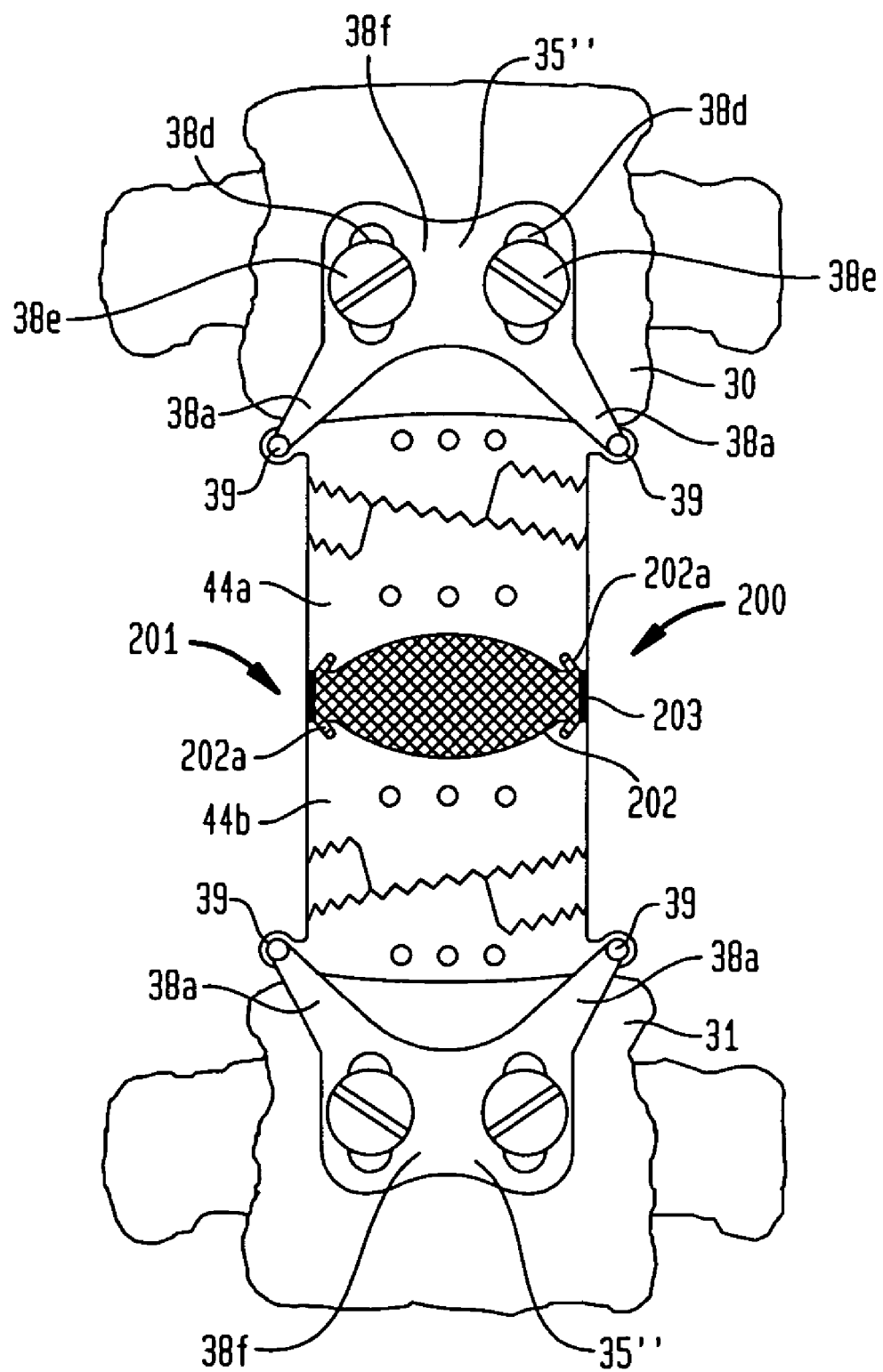
FIG. 22 is a rigid adjustable vertebral replacement implant system similar to the embodiment of FIG. 21 that provides flexibility, compressibility, and tiltability similar to the embodiment of FIG. 16.

FIG. 22 shows another rigid adjustable vertebral replacement implant 200 similar to implant 1B' of FIG. 21, except that implant 200 incorporates an artificial disc similar to the embodiment of FIG. 16 to provide rigidity after implantation and compressibility and motion preservation after osseous-integration has been achieved between implant 200 and adjacent vertebrae 30 and 31. In comparison with implant 1B' of FIG. 21, implant 200 comprises an additional component of an artificial disc 201 separating connecting tube 44 into upper connecting tube 44a and lower connecting tube 44b, similar to the one shown in FIG. 16 to provide compressibility and motion preservation. Alternatively, implant 200 is similar to the artificial disc of FIG. 16, with the upper and lower plate members 100 and 101 replaced with two cages 1B of FIG. 1.

Figure 23A:
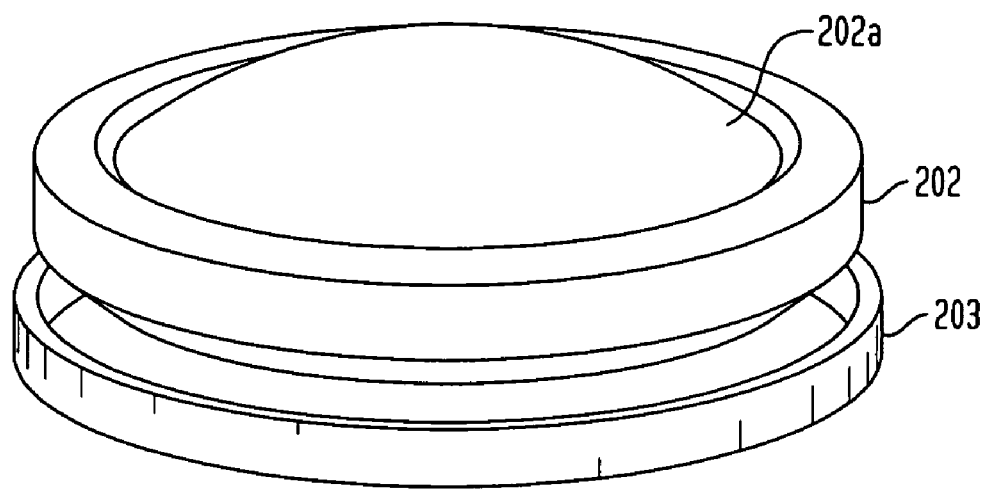
FIGS. 23A-B show an exploded view of the artificial disc portion of the rigid adjustable vertebral replacement implant system of FIG. 22.
Figure 23B:
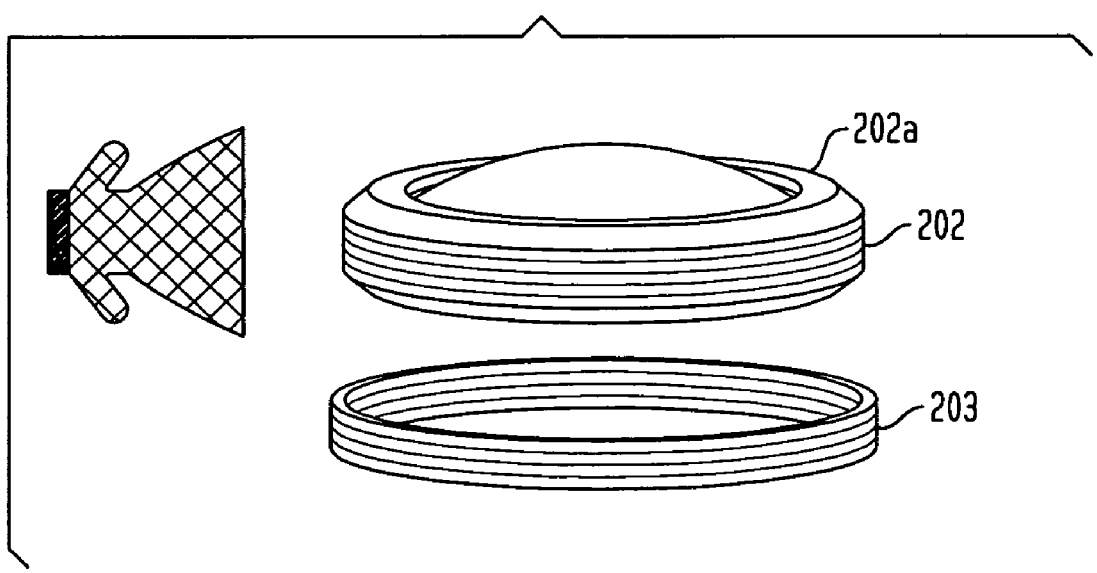

As shown in FIGS. 23A-B, the artificial disc 201 portion of the implant 200 comprises a convex flexible and compressible disc core 202. Disc core 202 may be made of titanium or some other known material which is biocompatible, flexible and compressible. At the perimeter of disc core 202 is a circular flange 202a extending towards the opposing convex surfaces of disc core 202. The circular flange 202a holds the upper and lower connecting tubes 44a and 44b together. A bio-resorbable rigid element 203 surrounds the disc core 202 to make the artificial disc 201 rigid in order to allow osseous-integration of the top and bottom sections 2B and 3B with the bones of the vertebrae 30 and 31. The upper and lower connecting tubes 44a and 44b have surfaces that correspond to the shape and size of disc core 202 and bio-resorbable rigid element 203. The bio-resorbable rigid element 203 will be resorbed and thereafter the flexible disc core 202 will function in a flexible, compressible, and tiltable manner for motion preservation between the vertebrae 30 and 31.

The connecting and stabilizing assembly 35" used with implant 200 is similar to the connecting and stabilizing assembly 35' of FIG. 21. One end of each of the pair of connecting rods 38a, is attached to a holding knob 39 which bears against the outer surfaces of the top and bottom sections 2B and 3B of implant 200. The opposite ends of each pair of connecting rods 38a joined to form a tab 38f, wider than tab 38c of FIG. 21. Tab 38f contains two slot openings 38d for receiving two screws 38e, respectively, or other suitable means for attaching the connecting and stabilizing assembly 35" to vertebrae 30 or 31. The two slot openings 38d allow more precise fine-tune positioning of the connecting and stabilizing assembly 35" before securing it with screws 38e to the vertebrae 30 or 31.

As a rigid adjustable vertebral intermediate body, implant 200 is inserted and adjusted as described above in connection with implant 1B' of FIG. 21. The rigidity of implant 200 is not compromised by the artificial disc portion 201 for a period of time after implantation due to the presence of the rigid bio-resorbable element 203 that prevents any compression, flexibility or motion of the artificial disc portion 201. Only after a period of time when osseous integration has been achieved that the artificial disc portion 201 of implant 200 provides flexibility, compressibility and/or tiltability for motion preservation.

Figure 24A:
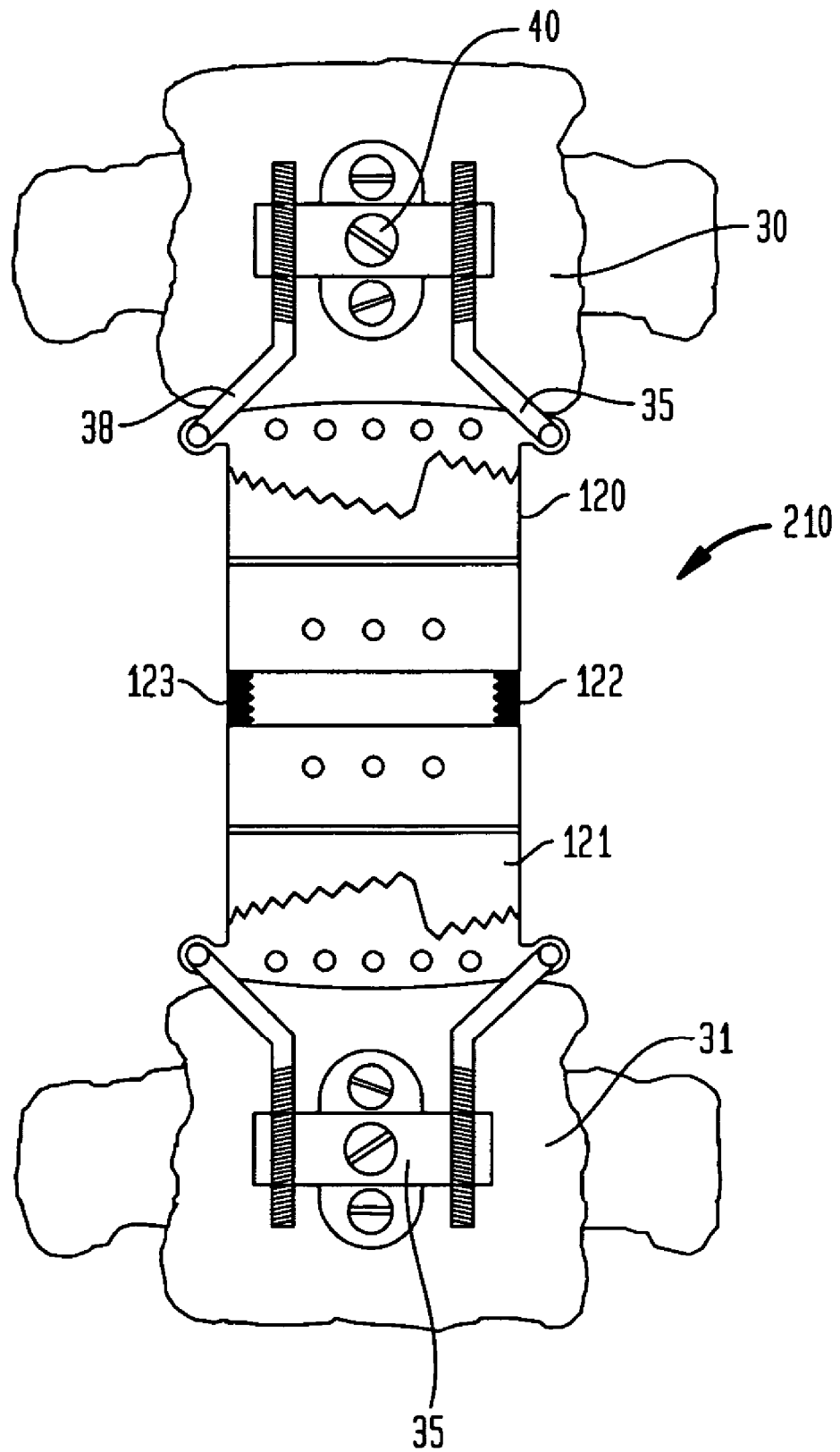
FIGS. 24A-B show the embodiments of FIGS. 17A and 17C being used as a rigid adjustable vertebral replacement implant system that connects to and stabilizes adjacent vertebrae.
Figure 24B:
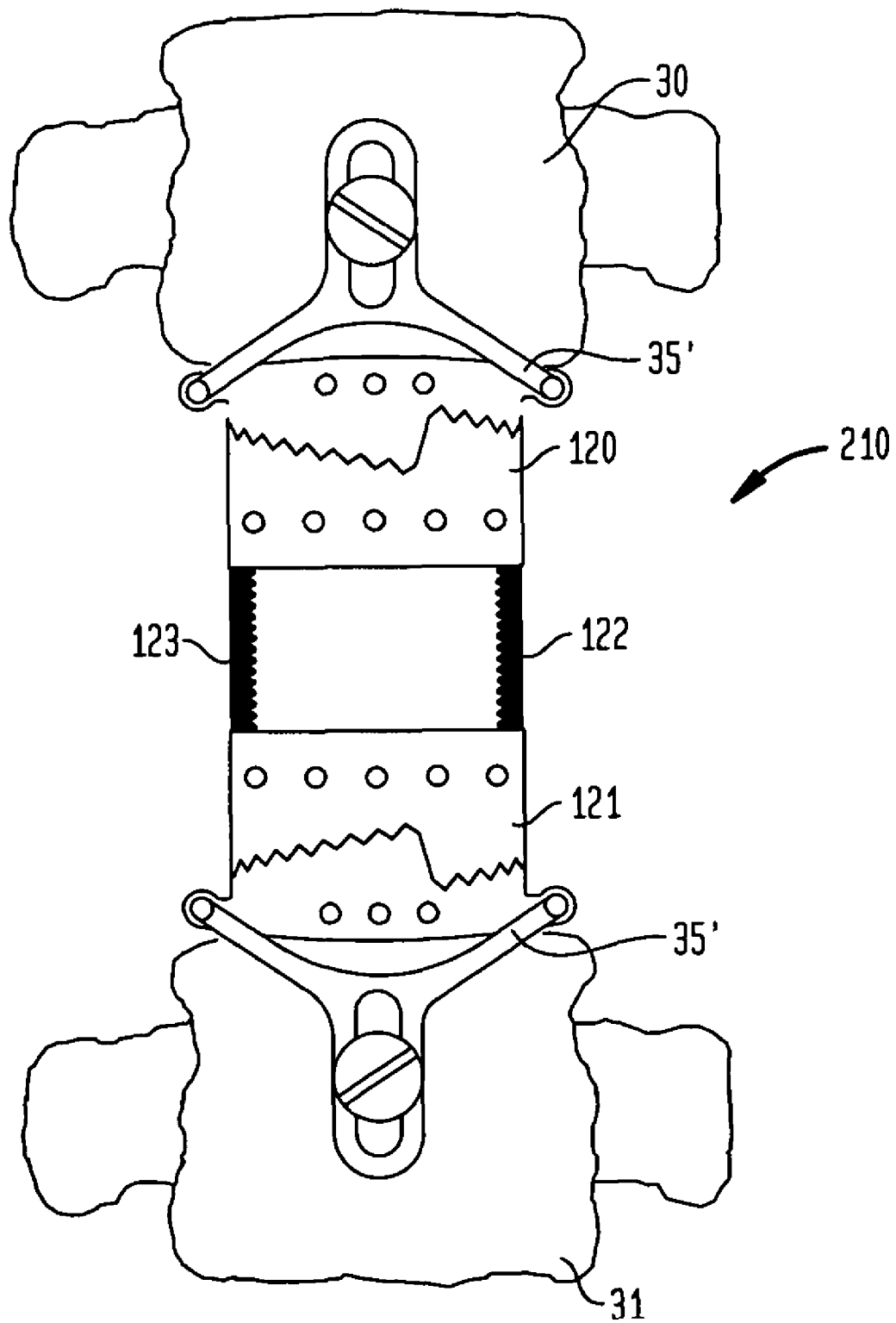

FIGS. 24A-B show the embodiments of FIGS. 17A and 17C being used as a vertebral replacement implant 210. Implant 210 is connected to adjacent vertebrae 30 and 31 with a connecting and stabilizing assembly 35 of FIG. 11A. Interposed between the pair of expandable cages 120 and 121 is a bellows-like assembly 122 and a resorbable rigid material 123 that provide rigidity after implantation and flexibility, compressibility and motion preservation after osseous-integration has been achieved, and the rigid material 123 resorbed, between implant 210 and adjacent vertebrae 30 and 31. While the resorbable material 123 is shown to surround the bellows 122, the bellows 122 may surround the resorbable material 123 also. The bellows-like assembly 122 is made of a bio-compatible material such as titanium. When first implanted, implant 210 is rigid due to the presence of the resorbable rigid material 123. Upon resorption of the rigid material 123, the bellows flexes to act as a cushion between the two cages 120 and 121 to provide compressibility and motion preservation. The inner volume of the bellows 122 may be filled with an elastomeric polymer, spring(s) or a combination of polymer and spring.

Figure 25:
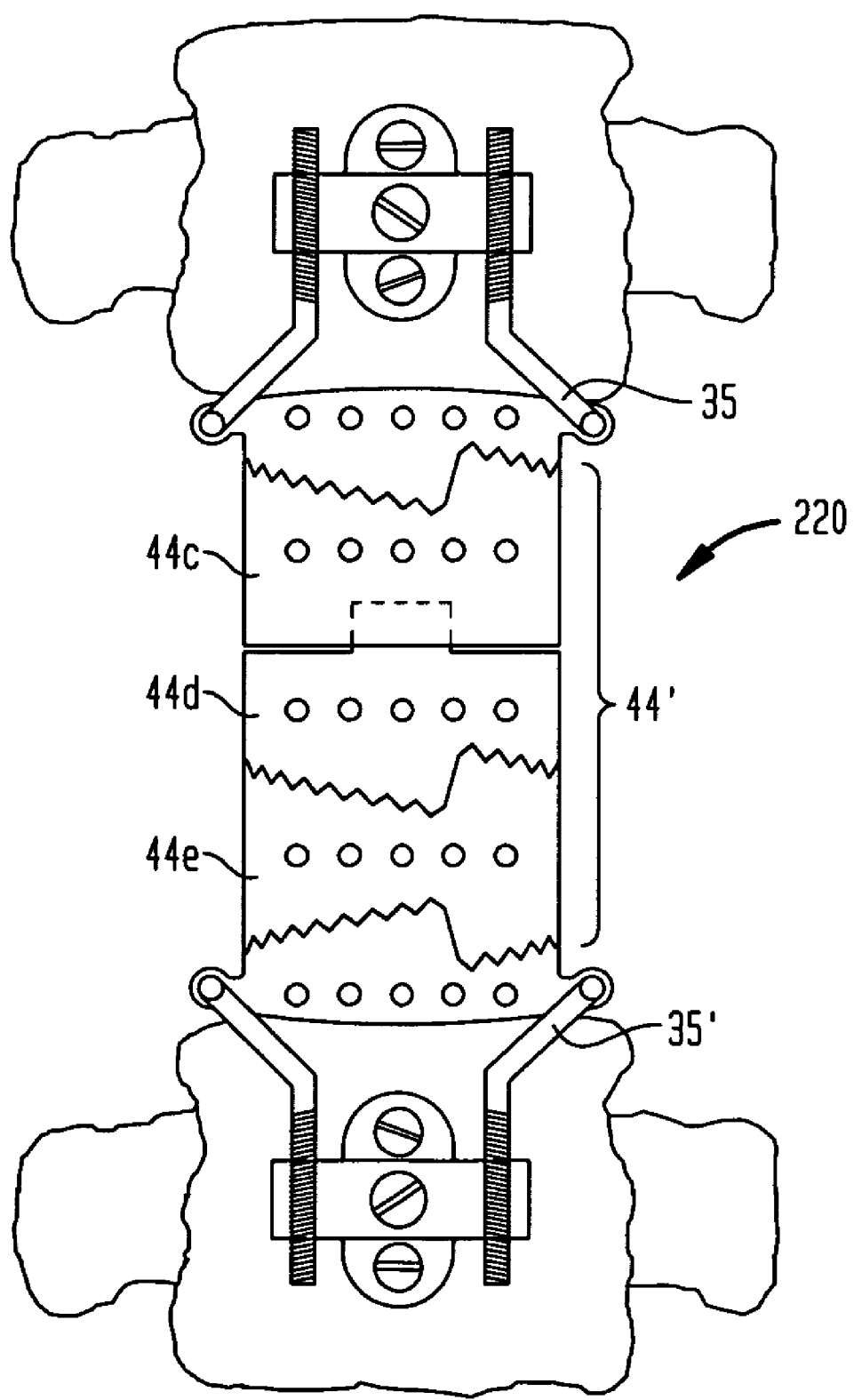
FIG. 25 is another rigid adjustable vertebral replacement implant system similar to the embodiment of FIG. 21.
Figure 26:
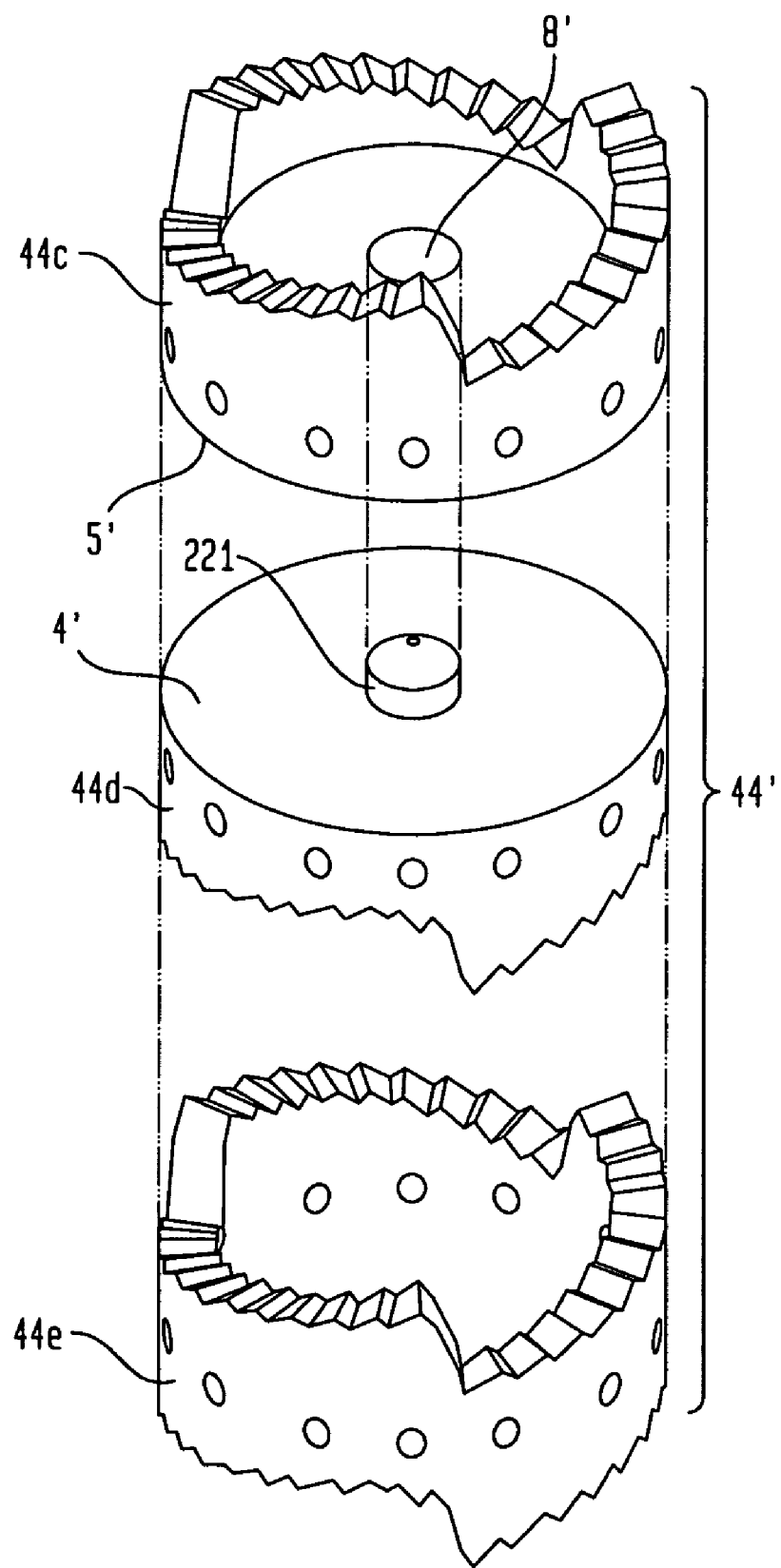
FIG. 26 is an exploded view of the connecting tube portion of the rigid adjustable vertebral replacement implant system of FIG. 25.

FIG. 25 is a rigid adjustable vertebral replacement implant 220 similar to cage 1B' of FIG. 21, connected to adjacent vertebrae 30 and 31 with a connecting and stabilizing assembly 35 of FIG. 11A. In comparison with connecting tube 44 of cage 1B', connecting tube 44' of implant 220 comprises of three sections 44c, 44d and 44e (see FIG. 26). Section 44c is similar to lower section 3 of cage 1 of FIG. 1, except that the bottom bearing surface 5' is smooth and the central opening 8' is larger for the purpose of receiving shaft 221 of section 44d. Section 44d is similar to upper section 2 of cage 1 of FIG. 1, except that the top bearing surface 4' is smooth. Section 44e is similar to the connecting tube 44 of FIG. 6. When assembled, sections 44c and 44d freely rotate with respect to each other along the axis of the shaft 221. Implant 220 allows the selective upper or lower adjustments of the vertebrae 30 and 31 by rotating different sections 44c, 44d or 44e of the connecting tube 44'.

Figure 27:
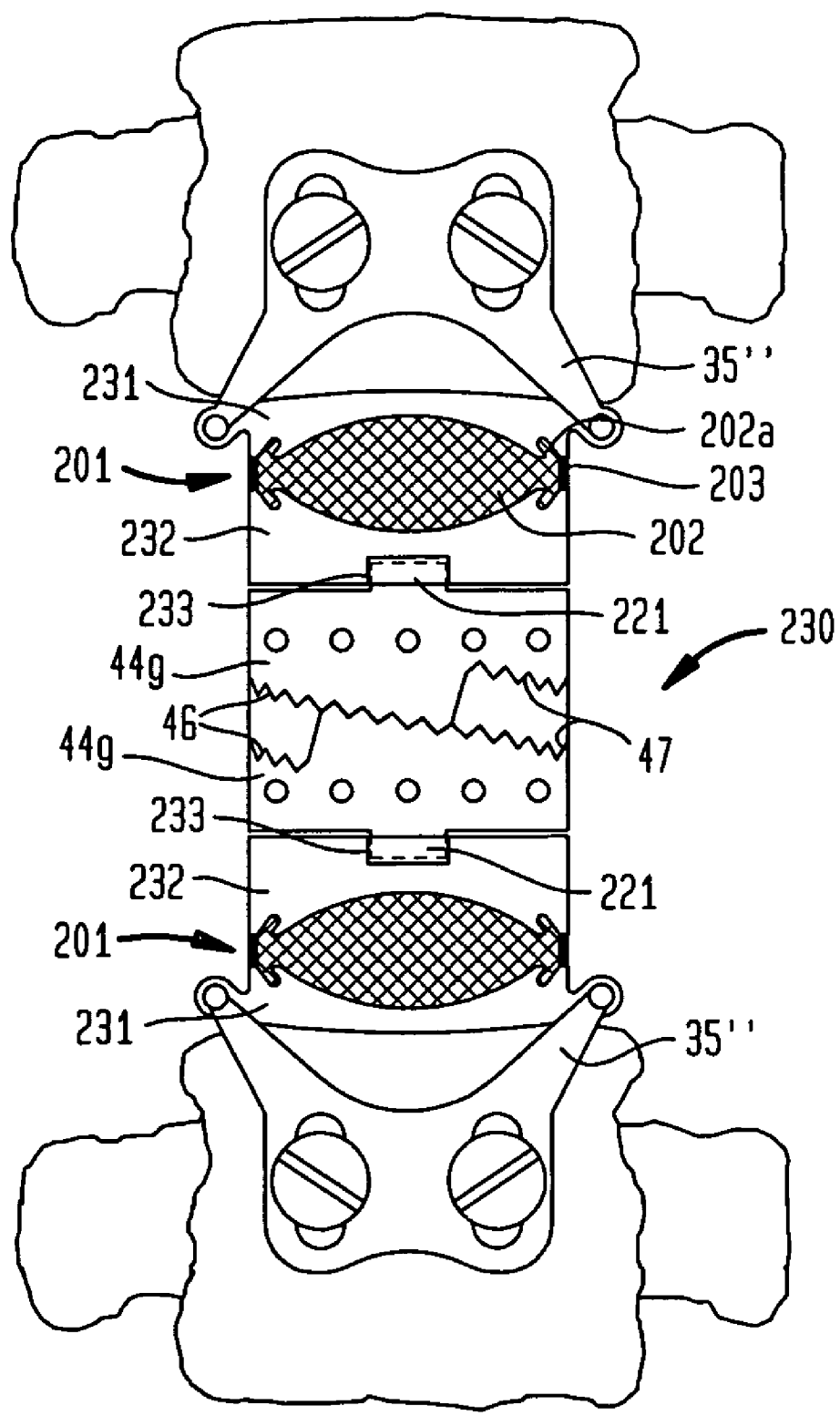
FIG. 27 is another rigid adjustable vertebral replacement implant system that provides flexibility, compressibility, and tiltability.

FIG. 27 is another rigid adjustable vertebral replacement implant 230 that provides flexibility, compressibility and tiltability by incorporating two artificial discs 201 of FIG. 22. Each artificial disc 201 is fixedly attached to outer and inner extensions 231 and 232, respectively. The outer and inner extensions 231 and 232 have surfaces that correspond to the artificial disc 201. The outer extension 231 is attached to vertebrae 30 or 31 with the connecting and stabilizing assembly 35". The inner extension 232 has a central opening 233 for receiving shaft 221 of section 44g, which is identical to section 44d of FIG. 26. The cam surfaces 46 of the two sections 44g face each other with the teeth 47 of the two sections 44g interfit with each other. The inner extensions 232 and sections 44d freely rotate with respect to each other along the axis of the shaft 221 to allow height adjustment of the implant 230 when the two sections 44g are rotated with respect to each other.

Figure 28:
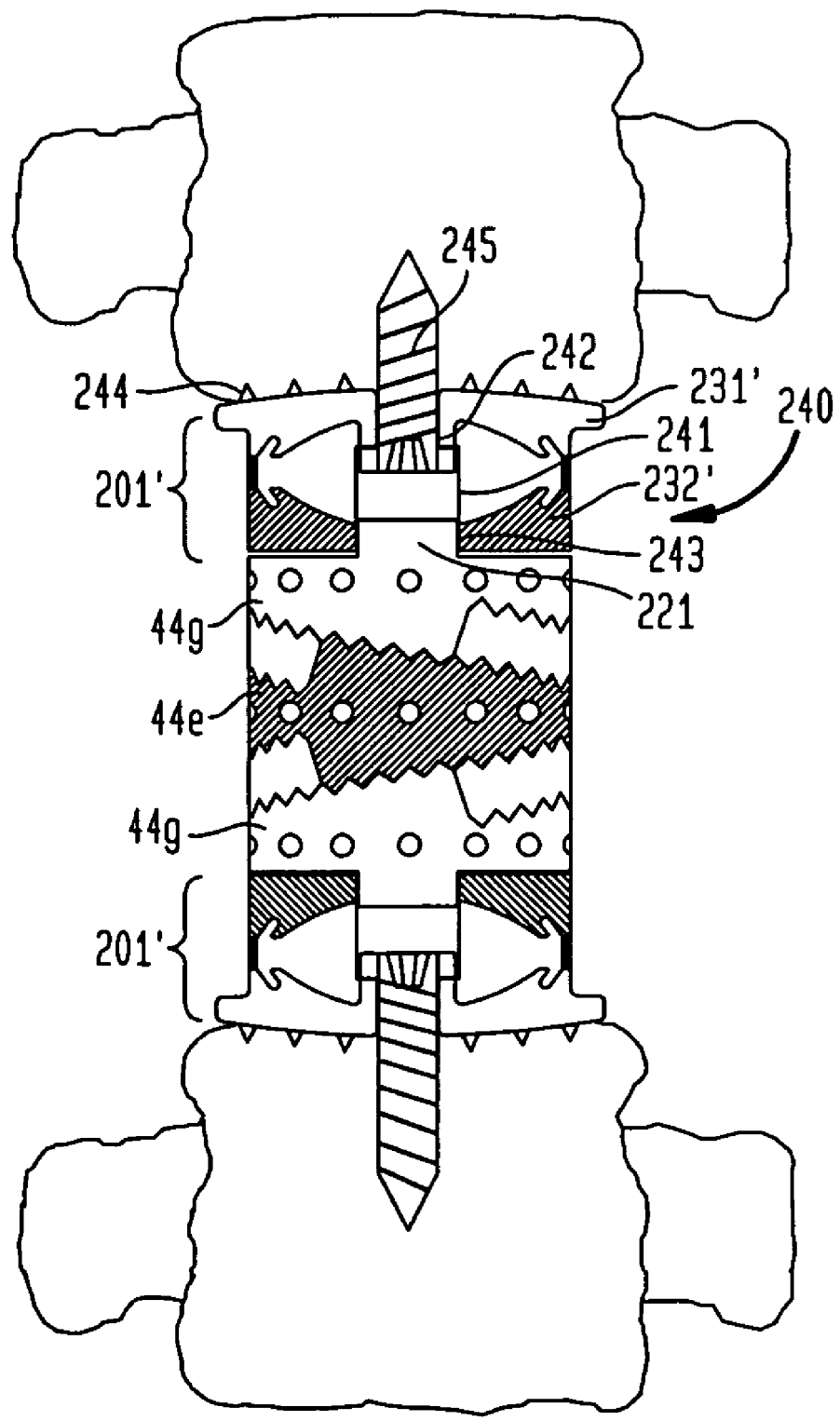
FIG. 28 is another rigid adjustable vertebral replacement implant system that provides flexibility, compressibility, and tiltability.

FIG. 28 is another rigid adjustable vertebral replacement implant 240 that provides flexibility, compressibility and tiltability by incorporating two artificial discs 201', similar to the artificial disc 201 of FIG. 22, except that artificial disc 201' has a central opening 241. Artificial disc 201' is fixedly attached to outer and inner extensions 231' and 232', respectively. Outer and inner extensions 231' and 232' are similar to outer and inner extensions 231 and 232 of FIG. 27, except that each has a central opening 242 and 243, respectively. The outer surface of the outer extension 231' may have spikes 244 for secure attachment to adjacent vertebrae 30 or 31. The artificial disc 201' and extensions 231' and 232' are securely attached to adjacent vertebrae 30 or 31 with a bio-compatible screw 245. The openings 241 and 243 are slightly wider than the head of screw 245, with the opening 242 smaller than the head of the screw 245 such that the screw 245 can securely fasten the artificial disc 201' and extensions 231' and 232' to vertebrae 30 or 31. Each opening 243 of inner extension 232' receives shaft 221 of section 44g such that section 44g can freely rotate with respect to inner extension 232'. The two sections 44g sandwich section 44e to form implant 240. Similar to implant 220, implant 240 allows the selective upper or lower adjustments of the vertebrae 30 and 31 by rotating different sections 44g or 44e.

Figure 29A:
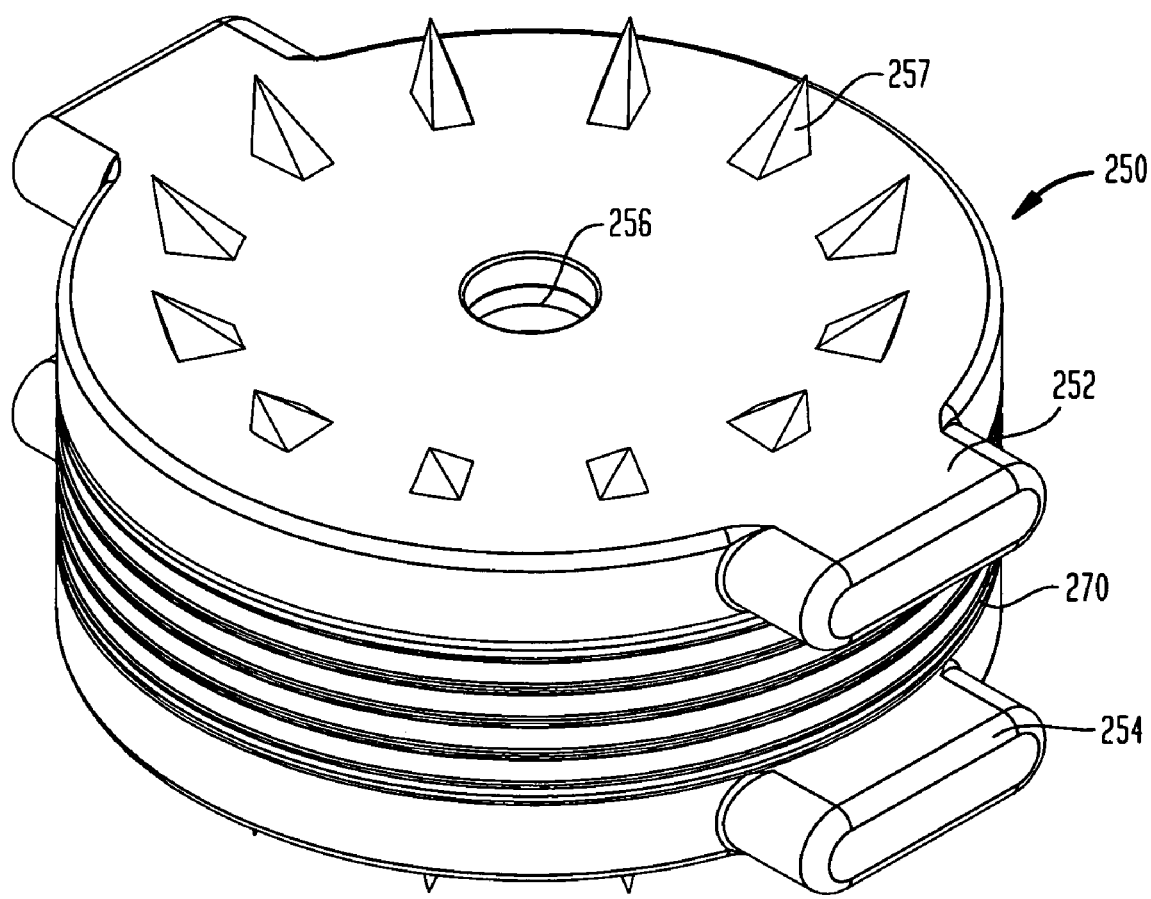
FIGS. 29A-B show another artificial disc that provides flexibility, compressibility, and tiltability that may be used with the rigid adjustable vertebral replacement implant system of the present invention.
Figure 29B:
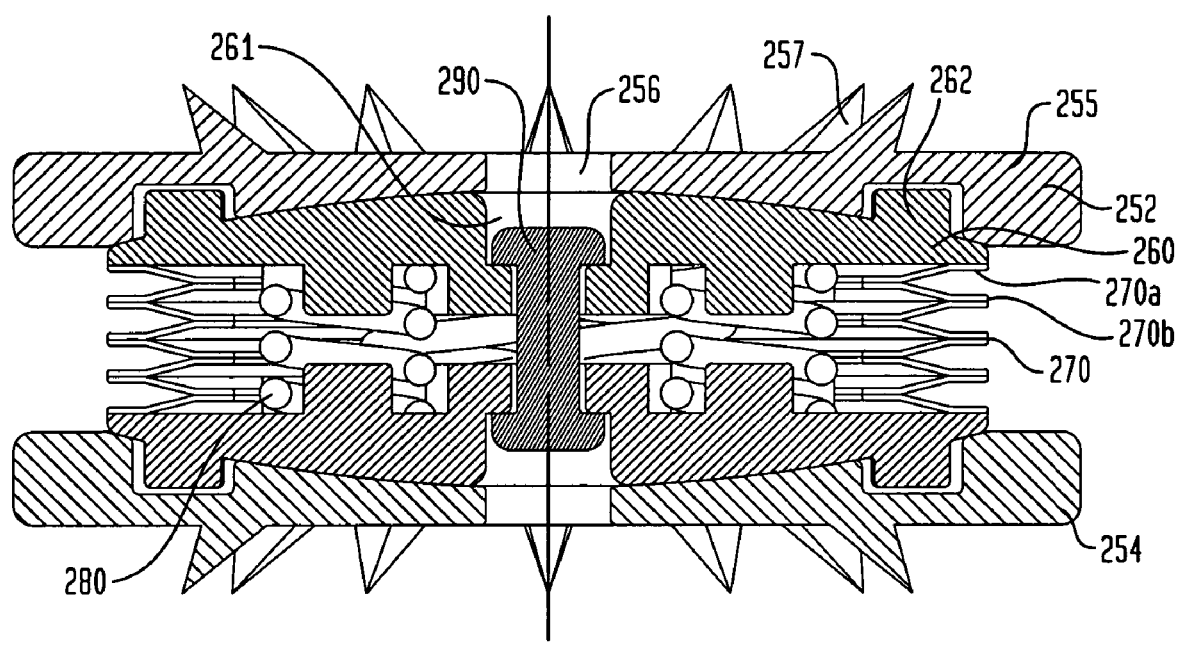

FIGS. 29A-B is another artificial disc 250 portion that may be used with the rigid adjustable vertebral replacement implant system of the present invention. The artificial disc 250 includes upper and lower sections 252 and 254, a disc core 260, a bellows-like element 270, a plurality of springs 280 and a holding element 290 that holds the disc core 260, bellows-like element 270 and plurality of springs 280 in place.

As shown in FIGS. 30A-D, the upper or lower section 252 and 254 is rigid, generally disc-shape, with opposing rectangular tab extensions 255 and a central opening 256. On the outer surface of the upper or lower section 252 or 254 is a plurality of spaced-apart spikes 257 forming a circle adjacent the perimeter of the disc-shape for attaching to adjacent vertebrae 30 or 31 or other components of the rigid adjustable vertebral replacement implant system. The outer surface of the upper or lower section 252 or 254 is shown to be substantially flat; however, it may have a concave or convex surface. On the inner surface of the upper or lower section 252 or 254 is a plurality of recesses 258. The plurality of recesses 258 are spaced apart and form a circle near the perimeter of the disc-shape upper or lower section 252 or 254. The inner surface of the upper or lower section 252 or 254 is shown to be concave; however, it may be substantially flat or convex.

Figure 31A:
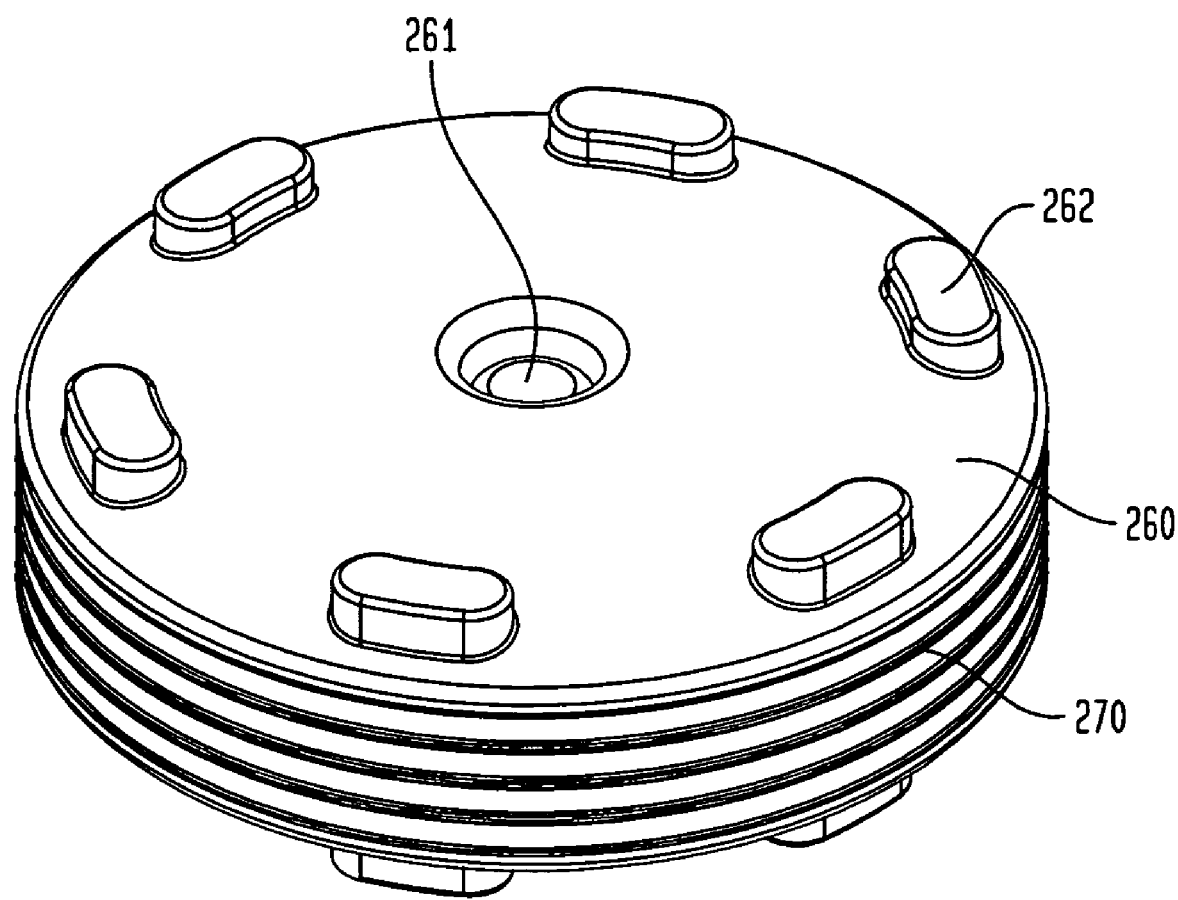
FIGS. 31A-B show the disc core and bellows-like element of the artificial disc of FIGS. 29A-B.
Figure 31B:
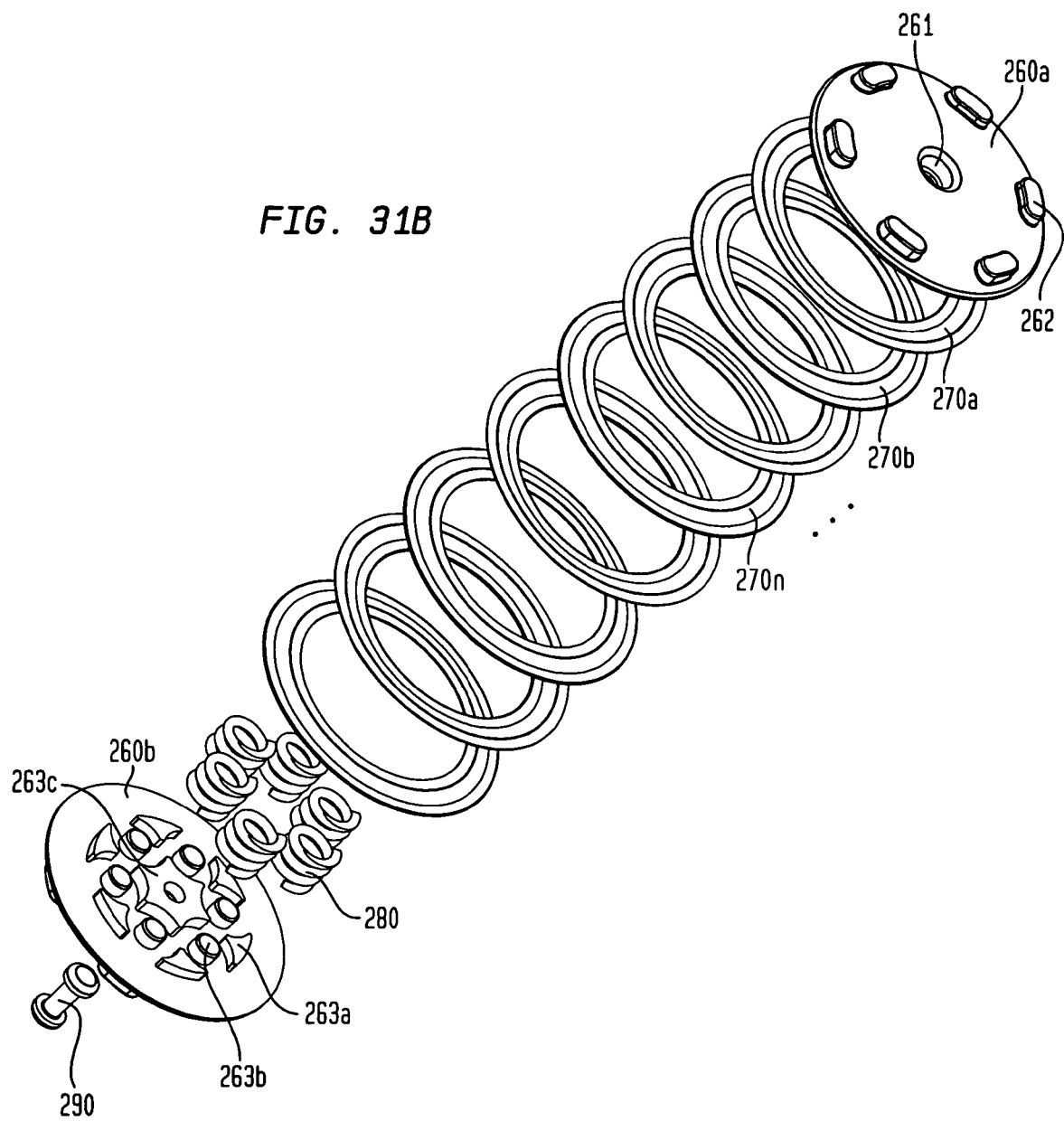

As shown in FIGS. 31A-B, the disc core 260 includes upper and lower elements 260a and 260b. Disc core 206 may be made of titanium or some other known material which is biocompatible, flexible and compressible. Each disc core element 260a or 260b has a central opening 261, and an outer surface that corresponds to the inner surface of the upper or lower section 252 or 254, i.e. convex and has a plurality of protrusions 262. The plurality of protrusions 262 are spaced apart and form a circle near the perimeter of the disc core element 260a or 260b. The inner surface of each disc core element 260a or 260b has a plurality of protrusions 263a, 263b and 263c for receiving and retaining the plurality of springs 280. The bellows-like element 270 includes a plurality of substantially uniformly thin, but non-planar, rings 270a, 270b . . . 270n that are stacked together to form the shape of a spring-like bellow. A holding element 290 inserted through the central opening 261 securely holds the upper and lower elements 260a and 260b to form the disc core 260, with the bellows-like element 270 and plurality of springs 280 therebetween. The plurality of protrusions 262 of the disc core elements 260a and 260b engages the plurality of recess 258 of the upper and lower sections 252 and 254, respectively.

Figure 32:
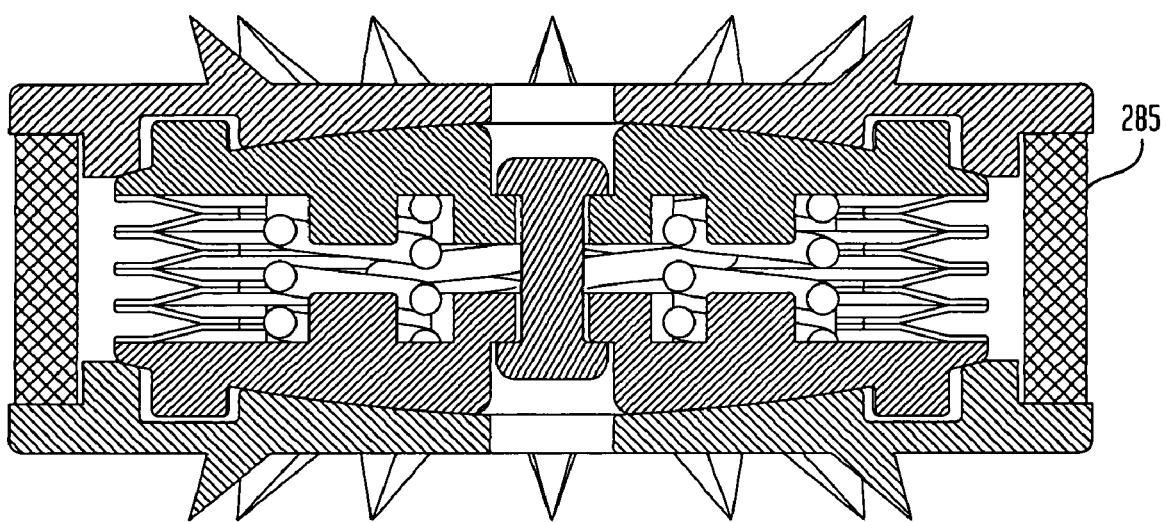
FIG. 32 shows the artificial disc of FIGS. 29A-B with a bio-resorbable material that temporarily prevents flexing, compressing or tilting of the artificial disc.

As shown in FIG. 32, artificial disc 250 may include a bio-resorbable rigid material 285 that temporarily prevents flexing, compressing or tilting of the artificial disc 250. Upon resorption of the rigid material 285, the disc core 260, bellow-like element 270, and springs 280 can then flexes, compresses and/or tilts for motion preservation. The bio-resorbable rigid material 285 is located between the corresponding rectangular tab extensions 255 of the upper and lower sections 252 and 254 adjacent the bellows-like element 270. The bio-resorbable material 285 can alternatively surrounds the bellows-like element 270. If desired, the space within or inside the bellows-like element 270 may be filled with an elastomeric polymer.

Figure 33:
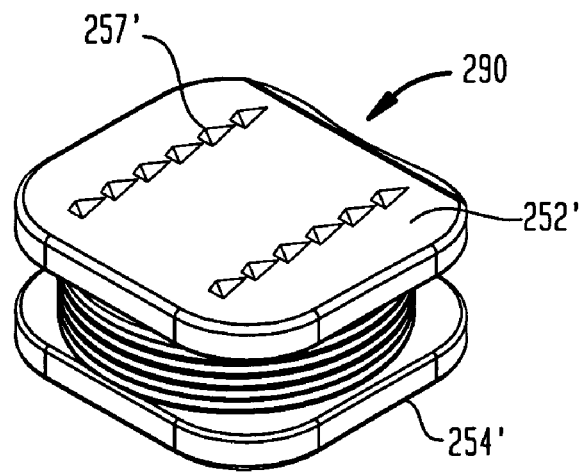
FIG. 33 shows another artificial disc that may be used with the rigid adjustable vertebral replacement implant system of the present invention.

FIG. 33 shows another artificial disc 290 that may be used with the rigid adjustable vertebral replacement implant system of the present invention. Artificial disc 290 is identical to artificial disc 250 of FIGS. 29A-B, except that the upper or lower section 252' and 254' is generally square-shape, and each has two rows of spikes 257'.

Figure 34:
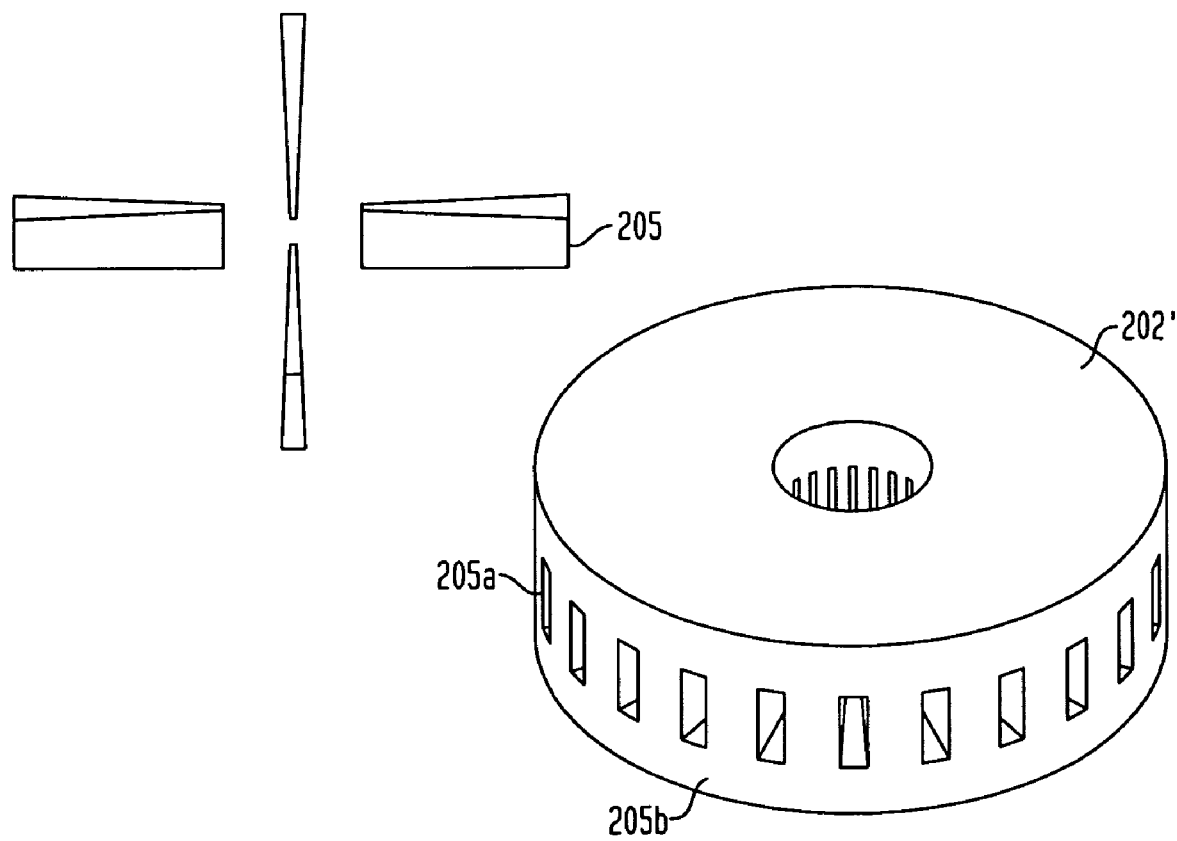
FIG. 34 shows an another disc core for the artificial disc portion of the rigid adjustable vertebral replacement implant system.

FIG. 34 shows another disc core 202' that can replace the disc core 202 shown in FIGS. 23A-B or the disc core 260 shown in FIGS. 31A-B in an artificial disc. Disc core 202' is formed with a plurality of radially extending wedges 205 sandwiched between top and bottom core elements 205a and 205b. Similar to the disc core 202 and 260, disc core 202' may be made of titanium, elastomer, or other known material which is biocompatible, flexible, and compressible.

It will thus be seen that the present invention provides improved means for achieving fusion of the inter-vertebral space and stabilization as a single procedure in a manner consistent with the conventional methods of discectomy or corpectomy and re-establishing the ideal and normal pre-existing disc inter-space or enlarged inter-vertebral space which is easier, quicker, safer, and entails less blood loss than other known means. The present invention also achieves one stage inter-space fusion and stabilization with minimal damage and less removal of bone from the surface of the adjacent vertebrae and establishes the normal and pre-existing inter-vertebral space in an easy, quick, safe and precise manner. In addition, the present invention provides a system and device of inter-vertebral arthrodesis and stabilization that allows for the inter-vertebral space to be adjustable and of variable sizes and with greater simplicity and accuracy than any other known means by the use of a modular prosthesis having similar and multiple attachments that allows for insertion through a small incision and to reconstitute the inter-space occupying device into a much larger spacing member so as to fit the contours of any inter-space without the need to sacrifice any vertebral bone. The prosthesis of the present invention provides for an implant that has means for osseous integration with the adjacent vertebrae which can also act as a shock absorber when extremely heavy forces are exerted upon it and which permits the reestablishment of normal lordosis or kyphosis of the spine in a simple and precise manner and provides a system and biocompatible material for inducing bone growth that can readily be shaped into a desired form.

The present invention also provides a biocompatible material and system for controlling hemostasis thereby enhancing osseous integration in individuals with abnormal clotting problems and may also act over a prolonged period of time to control post-operative bleeding. With this invention, post-operative pain and infection are controlled and application of anti-tumor drugs or radiation beads may be easily administered by being time released locally and/or in combination with systemic drugs for this purpose.

As many varied modifications of the subject matter of this invention will become apparent to those skilled in the art from the detailed description given hereinabove, it will be understood that the present invention is limited only as provided in the claims appended hereto.

The embodiments of the invention in which an exclusive property or privilege is claimed are defined as follows:

1. A height adjustable prosthetic system for placement between adjacent vertebrae comprising:
   at least one upper member and at least one corresponding lower member, each member having corresponding outer and inner bearing surfaces, each of said outer bearing surfaces adapted to face an adjacent vertebra;
   a connecting member interposed between each of said upper member and corresponding lower member, said connecting member having opposite first and second ends, each first end of said connecting member engages said inner bearing surface of said upper member and each second end of said connecting member engages said inner bearing surface of corresponding lower member;
   means for adjusting the height of said prosthetic system; and
   a connecting and stabilizing assembly adapted to attach each of said upper and lower members to an adjacent vertebra; and
   wherein said height adjusting means comprises:
   a plurality of inclined cam surfaces having teeth extending substantially vertically from the inner bearing surfaces of said upper and lower members;
   a plurality of inclined cam surfaces having teeth corresponding to said plurality of inclined cam surfaces of said upper and lower members on each of first and second ends of said connecting member;
   wherein relative movement of said inclined cam surfaces of said upper and lower members with said inclined cam surfaces of said connecting member increases or decreases the height of said prosthetic system; and
   further comprising means for maintaining said upper member in axial alignment with each first end of said connecting member and for maintaining said lower member in axial alignment with each second end of said connecting member, when the height of the prosthetic system is increased or decreased by relative movement of said inclined cam surfaces of said upper and lower members with said inclined cam surfaces of said connecting member.

2. The height adjustable prosthetic system of claim 1 wherein said upper and lower members and connecting member are substantially circular such that relative rotation of said upper and lower members with respect to said connecting member in opposite directions increases or decreases the height of said prosthetic system.

3. The height adjustable prosthetic system of claim 1 wherein said height adjusting means further comprises a plurality of openings on said upper and lower members and connecting member to facilitate movement of said upper and lower members with respect to said connecting member.

4. The height adjustable prosthetic system of claim 1 where said connecting and stabilizing assembly comprises:
   at least one holding knob adjacent said outer surfaces of said upper and lower members,
   at least one connecting rod having opposite ends, one end of each connecting rod attaches to said holding knob, the opposite end of each connecting rod having an opening;
   means for fastening said connecting and stabilizing assembly through said opening to said vertebrae.

5. The height adjustable prosthetic system of claim 4 wherein said fastening means comprises a bio-compatible screw.

6. The height adjustable prosthetic system of claim 1 wherein said connecting member further comprises: an the artificial disc interposed between said opposite ends of said connecting member provides flexibility, compressibility and tiltability to said prosthetic system.

7. The height adjustable prosthetic system of claim 6 wherein said artificial disc comprises:
   an upper element and a lower element;
   means for supporting said prosthetic system in a flexible, compressible and tiltable fashion between said upper and lower elements; and
   means for temporarily stabilizing said supporting means for a certain period of time to prevent flexibility, compressibility and tiltability of said prosthetic system.

8. The height adjustability prosthetic system of claim 7 wherein said artificial disc further comprises an elastomeric polymer between said upper and lower elements for additional support and motion preservation.

9. The height adjustability prosthetic system of claim 7 wherein said artificial disc further comprises at least one spring between said upper and lower elements for additional support and motion preservation.

10. The height adjustable prosthetic system of claim 7 wherein said supporting means comprises a disc core having opposing convex surfaces, a perimeter and a circular flange extending from said perimeter towards said opposing convex surfaces.

11. The height adjustable prosthetic system of claim 10 wherein said temporarily stabilizing means comprises a bio-resorbable rigid element surrounding said disc core.

12. The height adjustable prosthetic system of claim 7 wherein said supporting means comprises a disc core formed from a plurality of radially extending wedges sandwiched between top and bottom core elements.

13. The height adjustability prosthetic system of claim 8 wherein said artificial disc further comprises at least one spring between said upper and lower elements for additional support and motion preservation.

14. The height adjustable prosthetic system of claim 7 wherein said supporting means comprises a bellows-like element.

15. The height adjustable prosthetic system of claim 14 wherein said temporarily stabilizing means comprises a bio-resorbable rigid material surrounding said bellows-like element.

16. The height adjustable prosthetic system of claim 7 wherein said supporting means comprises an elastomeric polymer within a bellows like element.

17. The height adjustable prosthetic system of claim 7 where in said supporting means comprises a spring within a bellows like element.

18. The height adjustable prosthetic system of claim 1 wherein said connecting member comprises:
   a first element having inner and outer surfaces, said outer surface defining one end of said connecting member;
   a second element having inner and outer surfaces, said outer surface defining the opposite end of said connecting member; and
   a third element having opposing surfaces interposed between said first and second elements;
   wherein said inner surface of said first element is substantially flat and smooth and having a generally central opening;

wherein one surface of said third element adjacent said first element is substantially flat and smooth and having a generally central shaft extension for engaging said central opening of said first element to allow free rotation of said third element with respect to said first element, and said opposing surface of said third element having a plurality of inclined cam surfaces having teeth extending substantially vertically from said opposing surface;

wherein said inner surface of said second element having a plurality of inclined cam surfaces having teeth corresponding to said plurality of inclined cam surfaces of said third element such that relative movement of said inclined cam surfaces of said second and third elements increases or decreases the height of said prosthetic system.

19. The height adjustable prosthetic system of claim 1, wherein each of said upper and lower members comprises an artificial disc, each inner bearing surface of said artificial disc having a generally central opening;

said connecting means comprises an upper element and a lower element, each upper and lower element having an opposing surface facing each other, and outer surfaces defining the opposite ends of said connecting members, each outer surface of said upper and lower elements having a generally central shaft extension for engaging said generally central opening of said artificial disc; and said height adjusting means comprises a plurality of inclined cam surfaces having teeth extending substantially vertically from each opposing surface of said upper and lower elements, wherein relative movement of said inclined cam surfaces of said upper element with said inclined cam surfaces of said lower element increases or decreases the height of said prosthetic system.

20. The height adjustable prosthetic system of claim 19 wherein said artificial disc comprises:

means for supporting said prosthetic system in a flexible, compressible and tiltable fashion; and means for temporarily stabilizing said supporting means for a certain period of time to prevent flexibility, compressibility and tiltability of said prosthetic system.

21. The height adjustable prosthetic system of claim 20 wherein said supporting means comprises a disc core having opposing convex surfaces, a perimeter and a circular flange extending from said perimeter towards said opposing convex surfaces.

22. The height adjustable prosthetic system of claim 21 wherein said temporarily stabilizing means comprises a bioresorbable rigid element surrounding said disc core.

23. The height adjustable prosthetic system of claim 1 wherein each of said upper and lower members comprises an artificial disc having a central, through, opening;

said connecting means comprising:
a first element having inner and outer surfaces, said outer surface defining one end of said connecting member;
a second element having inner and outer surfaces, said outer surface defining the opposite end of said connecting member, and
a third element having opposing surfaces interposed between said first and second elements;

said height adjusting means comprises a plurality of inclined cam surfaces having teeth extending substantially vertically from said inner surfaces of said first and second elements and said opposing surfaces of said third element, wherein relative movement of said inclined cam surfaces of said first, second and third elements with respect to each other increases or decreases the height of said prosthetic system, and said connecting and stabilizing assembly comprises a biocompatible screw inserted through said opening of said artificial disc to said vertebrae.

* * * * *